United States Patent [19]

Maloy

[11] Patent Number: 5,792,831
[45] Date of Patent: Aug. 11, 1998

[54] ANALOGUES OF MAGAININ PEPTIDES CONTAINING D-AMINO ACIDS

[75] Inventor: W. Lee Maloy, Lansdale, Pa.

[73] Assignee: Magainin Pharmaceuticals Inc., Plymouth Meeting, Pa.

[21] Appl. No.: 343,882

[22] Filed: Nov. 17, 1994

Related U.S. Application Data

[63] Continuation of Ser. No. 133,740, Oct. 5, 1993, abandoned, which is a continuation-in-part of Ser. No. 874,685, Apr. 28, 1992, abandoned, which is a continuation-in-part of Ser. No. 522,688, May 14, 1990, abandoned, which is a continuation-in-part of Ser. No. 476,629, Feb. 8, 1990, abandoned.

[51] Int. Cl.$^6$ ..................................................... A61K 38/16
[52] U.S. Cl. ................... 530/326; 514/13; 514/14
[58] Field of Search ................. 514/13, 14; 530/326

[56] References Cited

U.S. PATENT DOCUMENTS

| | | | |
|---|---|---|---|
| 4,107,298 | 8/1978 | Luning | 424/177 |
| 4,447,356 | 5/1984 | Olivera | 260/112.5 |
| 4,617,149 | 10/1986 | DiMarchi et al. | 530/324 |
| 4,636,489 | 1/1987 | Seemuller et al. | 514/12 |
| 4,659,692 | 4/1987 | Lehcer et al. | 514/12 |
| 4,668,662 | 5/1987 | Tripier | 514/12 |
| 4,791,100 | 12/1988 | Kramer et al. | 514/12 |
| 4,962,277 | 10/1990 | Cuervo et al. | 514/14 |
| 5,093,317 | 3/1992 | Lewis | 514/12 |
| 5,208,220 | 5/1993 | Berkowitz | 514/13 |

FOREIGN PATENT DOCUMENTS

| | | |
|---|---|---|
| 11290 | 11/1989 | WIPO. |
| WO 90/11771 | 4/1990 | WIPO. |

OTHER PUBLICATIONS

Gibson et al. J Biol. Chem. vol. 261 pp. 5341–5349 (1986).
Giovannini et al Biochem of vol. 243, pp. 113–120 (1987).
Burgen J Biol Chem 193, 13, 1951.
Docherty Antimicrob Agent Chemo Ther 31, 1562, 1987.
Coy BBRC 73, 632, 1976.
D. Wade et al., "All D-amino acid–containing channel forming antibiotic peptides," Proc. Natl. Acad. Sci., USA 87:4761–5 (1990).
von K. Vogler, et al., "Synthese von All–D–Val$^5$–Angiotensin II–Asp$^1$–β–Amid$^2$", vol. 48, Fasciculus 6 (1985) No. 152, pp. 1407–1414.
Journal of the American Chemical Society, "The Synthesis of $_D$–Oxytocin, the Enantiomer of the Posterior Pituitary Hormone, Oxytocin$^1$," vol. 87, 1965, Jul.–Sep., pp. 3775–3776.

*Primary Examiner*—David Lukton
*Attorney, Agent, or Firm*—Finnegan, Henderson, Farabow, Garrett & Dunner, L.L.P.

[57] ABSTRACT

Biologically active analogues of magainin peptides wherein each amino acid residue of the peptide is a D-amino acid residue or a glycine residue. Examples of such peptides wherein each amino acid residue is a D-amino acid residue or a glycine residue include deletion and substitution analogues of magainin peptides. Such peptides have increased resistance to proteolytic enzymes while retaining biological activity.

8 Claims, 1 Drawing Sheet

ANALOGUES OF MAGAININ PEPTIDES CONTAINING D-AMINO ACIDS

This application is a continuation, of application Ser. No. 08/133,740 filed Oct. 5, 1993, now abandoned; which is a continuation-in-part of application Ser. No. 07/874,685, filed Apr. 28, 1992, now abandoned; which is a continuation-in-part of application Ser. No. 07/522,688, filed May 14, 1990, now abandoned which is a continuation-in-part of application Serial No. 07/476,629 filed Feb. 8, 1990, now abandoned.

BACKGROUND OF THE INVENTION

This invention relates to biologically active peptides, and more particularly to biologically active peptides wherein each amino acid residue of such peptides is a D-aimino acid residue or glycine.

SUMMARY OF THE INVENTION

In accordance with an aspect of the present invention, there is provided compound comprising an analogue of Magainin I Peptide or Magainin II peptide. Each amino acid residue of the Magainin I peptide and the Magainin II peptide is a D-amino acid residue or glycine. The Magainin I or Magainin II peptide is in an amide or carboxy terminated form. Magainin I is represented by the following structural formula using the single letter amino acid code and the numbers below each amino acid residues refer to the position of the residue in the peptide.

```
G I G K F L H S A G K F G
1 2 3 4 5 6 7 8 9 10 11 12 13
                              K A F V G E I M K S
                              14 15 16 17 18 19 20 21 22 23
```

Magainin II is represented by the following structural formula using the single letter amino acid code and the numbers below each amino acid residue refer to the position of the residue in the peptide:

```
G I G K F L H S A K K F G
1 2 3 4 5 6 7 8 9 10 11 12 13
                              K A F V G E I M N S
                              14 15 16 17 18 19 20 21 22 23
```

The Magainin I or Magainin II peptide is substituted in at least one of positions 1–23. The substituents which may be employed in each of positions 1–23 are shown in the following table:

| Residue No. | Substituent |
|---|---|
| 1 | D-Lys, D-Ala |
| 2 | D-Lys, D-Ala, D-Ile, D-Arg, D-Leu, D-Val, D-His, D-Met |
| 3 | D-Lys, D-Ala, D-Trp, D-Arg, D-His |
| 4 | D-Lys, D-Ala, D-Arg, D-His |
| 5 | D-Phe, D-Ala, D-Lys, D-Trp, D-Leu, D-Ile, D-Val, D-Met |
| 6 | D-Leu, D-Lys, D-Ala, D-Ile, D-Val , D-Met |
| 7 | D-Lys, D-His, D-Ala, D-Arg, D-Ile, D-Val, D-Met |
| 8 | D-Ala, D-Lys, D-Ser, D-Trp, D-Met, D-Ile, D-Arg, D-His, D-Thr, D-Leu, D-Val |
| 9 | D-Lys, D-Ala, D-Trp, D-Arg, D-His, D-Leu, D-Ile, D-Val |
| 10 | D-Lys, D-Ala, D-Trp, D-Arg, D-His , D-Leu, D-Ile , D-Val |
| 11 | D-Lys, D-Arg, D-His |
| 12 | D-Phe, D-Lys, D-Trp, D-Arg, D-His |
| 13 | D-Ala, D-Lys, D-Trp, D-Met, D-Arg, D-His, D-Phe, D-Leu, D-Ile, D-Val |
| 14 | D-Ala, D-Lys, D-Arg, D-His |
| 15 | D-Lys, D-Trp, D-Ala, D-Arg, D-His, D-Phe |
| 16 | D-Ala, D-Lys, D-Phe, D-Ile, D-Val, D-Met, D-Leu |
| 17 | D-Ala, D-Lys, D-Val, D-Trp, D-Arg, D-His, D-Met, D-Leu |
| 18 | D-Ala, D-Lys, D-Trp, D-Arg, D-His, D-Leu, D-Met |
| 19 | D-Ala, D-Lys, D-Glu, Gly, D-Arg, D-His, D-Leu D-Ile, D-Phe, D-Asn |
| 20 | D-Ile, D-Ala, D-Lys, D-Trp, D-Leu, D-Phe, D-Val, D-Met |
| 21 | D-Lys, D-Pro, D-Ala, D-His, D-Leu, D-Arg, D-Ile, D-Phe |
| 22 | D-Lys, D-Ala, D-Asn, D-Gln, D-Arg, D-His |
| 23 | D-Ser, D-Lys, D-Ala, D-Thr, Gly, D-Leu, D-Ile, D-Gln, D-Asn |

Preferably, the substituents are as follows:

| Residue No. | Substituent |
|---|---|
| 1 | D-Lys, D-Ala |
| 2 | D-Lys, D-Ala, D-Ile |
| 3 | D-Lys, D-Ala, D-Trp |
| 4 | D-Lys, D-Ala |
| 5 | D-Phe, D-Ala, D-Lys, D-Trp |
| 6 | D-Leu, D-Lys, D-Ala |
| 7 | D-Lys, D-His, D-Ala |
| 8 | D-Ala, D-Lys, D-Ser, D-Trp |
| 9 | D-Lys, D-Ala, D-Trp |
| 10 | D-Lys, D-Ala, D-Trp |
| 11 | D-Lys |
| 12 | D-Phe, D-Lys, D-Trp |
| 13 | D-Ala, D-Lys, D-Trp |
| 14 | D-Ala, D-Lys |
| 15 | D-Lys, D-Trp, D-Ala |
| 16 | D-Ala, D-Lys, D-Phe |
| 17 | D-Ala, D-Lys, D-Val, D-Trp |
| 18 | D-Ala, D-Lys, D-Trp |
| 19 | D-Ala, D-Lys, D-Glu |
| 20 | D-Ile, D-Ala, D-Lys, D-Trp |
| 21 | D-Lys, D-Pro, D-Ala |
| 22 | D-Lys, D-Ala, D-Asn |
| 23 | D-Ser, D-Lys, D-Ala |

It is to be understood that for purposes of the present invention, that the D-tryptophan residues may be protected with a formyl group or be unprotected. The D-phenylalanine residues, whether such residue is present in its normal position, or employed as a substitution residue, may be a normal D-phenylalanine residue or an iodinated D-phenylalanine residue.

DESCRIPTION OF THE PREFERRED EMBODIMENT

In accordance with one embodiment, the peptide is a Magainin I peptide, and at least one of amino acid residues 8, 10, 13, 16, 18 and 19 is substituted with a D-alanine residue. In another embodiment, the Magainin I peptide has D-alanine residue substitutions at each of amino acid residues 3, 8, 16, 19 and 23.

In accordance with another embodiment, the Magainin I peptide has D-alanine residue substitutions at four of amino acid residues 3, 8, 16, 19 and 23, and the remaining one of these residues is substituted with a D-lysine residue In accordance with yet a further embodiment, amino acid 21 of a Magainin I peptide is substituted with a D-proline residue.

In accordance with another embodiment, at least one of amino acid residues 3, 7, 8, 10, 18–21, and 23 of Magainin I is substituted with a D-lysine residue.

In accordance with another embodiment, amino acid residues 3, 8, 9, 19 and 23 of Magainin I are each substituted with a D-lysine residue and amino acid residue 16 is substituted with a D-alanine residue.

In accordance with a further embodiment, at least one of amino acid residues 3, 5, 8, 10, 12, 13, 15, 18, and 20 of Magainin I is substituted with a protected D-tryptophan residue, wherein the protecting group is preferably a formyl group. In accordance with another embodiment, at least one of amino acid residues 9, 13, 15 and 17 of Magainin I is substituted with an unprotected D-tryptophan residue.

In accordance with another embodiment, the peptide is a Magainin II peptide, and at least one of amino acid residues 1–8, 10, 13, 14, 16 and 18–23 is a D-alanine residue.

In accordance with another embodiment, at least one of amino acid residues 1–3, 5–9, 12, 13 and 15–23 of Magainin II is a D-lysine residue.

In accordance with another aspect of the present invention, there is provided an analogue of Magainin I or Magainin II peptide, said Magainin I or Magainin II peptide being in an amide- or carboxy-terminated form and having the structural formulas hereinabove described, wherein each amino acid residue of said Magainin I or Magainin II peptide is a D-amino acid residue or glycine, and wherein at least one of amino acid residues 15–23 is omitted and at least one of the remaining amino acid residues is substituted. The substituents which may be employed in at least one of positions 1–23 are shown in the following table:

| Residue No. | Substituent |
|---|---|
| 1 | D-Lys, D-Ala |
| 2 | D-Lys, D-Ala, D-Ile, D-Arg, D-Leu, D-Val, D-His, D-Met |
| 3 | D-Lys, D-Ala, D-Trp, D-Arg, D-His |
| 4 | D-Lys, D-Ala, D-Arg, D-His |
| 5 | D-Phe, D-Ala, D-Lys, D-Trp, D-Leu, D-Ile, D-Val, D-Met |
| 6 | D-Leu, D-Lys, D-Ala, D-Ile, D-Val, D-Met |
| 7 | D-Lys, D-His, D-Ala, D-Arg, D-Ile, D-Val, D-Met |
| 8 | D-Ala, D-Lys, D-Ser, D-Trp, D-Met, D-Ile, D-Arg, D-His, D-Thr, D-Leu, D-Val |
| 9 | D-Lys, D-Ala, D-Trp, D-Arg, D-His, D-Leu, D-Ile, D-Val |
| 10 | D-Lys, D-Ala, D-Trp, D-Arg, D-His, D-Leu, D-Ile, D-Val |
| 11 | D-Lys, D-Arg, D-His |
| 12 | D-Phe, D-Lys, D-Trp, D-Arg, D-His |
| 13 | D-Ala, D-Lys, D-Trp, D-Met, D-Arg, D-His, D-Phe, D-Leu, D-Ile, D-Val |
| 14 | D-Ala, D-Lys, D-Arg, D-His |
| 15 | D-Lys, D-Trp, D-Ala, D-Arg, D-His, D-Phe |
| 16 | D-Ala, D-Lys, D-Phe, D-Ile, D-Val, D-Met, D-Leu |
| 17 | D-Ala, D-Lys, D-Val, D-Trp, D-Arg, D-His, D-Met, D-Leu |
| 18 | D-Ala, D-Lys, D-Trp, D-Arg, D-His, D-Leu, D-Met, D-Phe |
| 19 | D-Ala, D-Lys, D-Glu, Gly, D-Arg, D-His, D-Leu, D-Ile, D-Phe, D-Asn |
| 20 | D-Ile, D-Ala, D-Lys, D-Trp, D-Leu, D-Phe, D-Val, D-Met |
| 21 | D-Lys, D-Pro, D-Ala, D-His, D-Leu, D-Arg, D-Ile, D-Phe |
| 22 | D-Lys, D-Ala, D-Asn, D-Gln, D-Arg, D-His |
| 23 | D-Ser, D-Lys, D-Ala, D-Thr, Gly, D-Leu, D-Ile, D-Gln, D-Asn |

Preferably, the substituents are as follows:

| Residue No. | Substituent |
|---|---|
| 1 | D-Lys, D-Ala |
| 2 | D-Lys, D-Ala, D-Ile |
| 3 | D-Lys, D-Ala, D-Trp |
| 4 | D-Lys, D-Ala |
| 5 | D-Phe, D-Ala, D-Lys, D-Trp |
| 6 | D-Leu, D-Lys, D-Ala |

-continued

| Residue No. | Substituent |
|---|---|
| 7 | D-Lys, D-His, D-Ala |
| 8 | D-Ala, D-Lys, D-Ser, D-Trp |
| 9 | D-Lys, D-Ala, D-Trp |
| 10 | D-Lys, D-Ala, D-Trp |
| 11 | D-Lys |
| 12 | D-Phe, D-Lys, D-Trp |
| 13 | D-Ala, D-Lys, D-Trp |
| 14 | D-Ala, D-Lys |
| 15 | D-Lys, D-Trp, D-Ala |
| 16 | D-Ala, D-Lys, D-Phe |
| 17 | D-Ala, D-Lys, D-Val, D-Trp |
| 18 | D-Ala, D-Lys, D-Trp |
| 19 | D-Ala, D-Lys, D-Glu |
| 20 | D-Ile, D-Ala, D-Lys, D-Trp |
| 21 | D-Lys, D-Pro, D-Ala |
| 22 | D-Lys, D-Ala, D-Asn |
| 23 | D-Ser, D-lys, D-Ala |

In accordance with a particular embodiment, amino acid residues 16–23 of Magainin I are deleted, and amino acid residues 3, 8 and 10 are substituted with a D-alanine residue.

In accordance with yet another embodiment, amino acid residue 19 of Magainin I is deleted, and preferably amino acid residues 5, 8, 9 and 16 are each substituted with a D-lysine residue, amino acid residue 21 is substituted with a D-leucine residue, and amino acid residues 18 and 23 are substituted with a D-alanine residue.

In accordance with another embodiment, in carboxy- or amide-terminated (preferably amide-terminated) Magainin I or Magainin II peptide, amino acid residues 17–23 or 16–23 or 15–23 are deleted, and amino acid residues 3, 7, and 8 are each substituted with a D-lysine residue, and optionally amino acid residue 13 and/or amino acid residue 10 is substituted with a D-alanine residue. Preferred peptides are as follows:

GIKKFLKKAGKFGK-NH$_2$

GIKKFLKKAGKFGKAF-NH$_2$

GIKKFLKKAKKFGKA-NH$_2$

GIKKFLKKAKKFAKA-NH$_2$

GIKKFLKKAAKFAKA-NH$_2$

Preliminary studies indicate that the above-mentioned preferred peptides possess low hemolytic activity. In accordance with a further embodiment, amino acid residue 21 of Magainin I may be deleted, and preferably amino acid residues 5, 10, 18, and 19 are each substituted with a D-lysine residue, amino acid residue 7 is substituted with a D-phenylalanine residue, and amino acid residue 22 is substituted with a D-alanine residue.

In accordance with another embodiment, in carboxy or amide terminated (preferably amide terminated) Magainin I or Magainin II (perferably Magainin II), amino acid residue 19 is omitted, and at least one of amino acid residues 3, 7, 8, 10, 13, 15, 16, 18 21, 22 or 23 is substituted with another amino acid as follows:

| Residue number | Subtituent |
|---|---|
| 3 | D-Leu |
| 7 | D-Lys |
| 8 | D-Lys, D-Ala |
| 10 | D-Ala, D-Lys |
| 13 | D-Trp, D-Leu, D-Phe, D-Ala |
| 15 | D-Phe |
| 16 | D-Ala |
| 18 | D-Lys, D-Ala, D-Phe |

-continued

| Residue number | Subtituent |
| --- | --- |
| 21 | D-Lys, D-Ile |
| 22 | D-Lys |
| 23 | D-Lys, D-Ser |

In a preferred embodiment, the peptide is a Magainin II peptide, and the substitution analogue wherein amino acid 19 is deleted is selected from the class consisting of the following substitution analogues:

GIGKFLKKAKKFGKAFVKILKK;
GIGKFLKSAKKFGKAFVKIMNS;
GIGKFLKKAKKFGKAFVKIMKK;
GIGKFLKSAKKFGKAFVKILNS;
GIGKFLKKAKKFAKAFVKIINN;
GIGKFLHSAKKFGKAFVGIMKS;
GIGKFLHSAKKFGKAFVAIMKS;
GIGKFLHSAKKFFKAFVFIMNS;
GIGKFLKSAKKFGKAFVFIMNS;
GIGKFLHKAKKFAKAFVFIMNS;
GIGKFLKSAKKFAKAFVFIMNS;
GIGKFLHKAKKFAKAFVFIMNK;
GIGKFLKKAKKFGKAFVFIMKK; and
GIGKFLHSAKKFGKAFVK**IMNS; wherein
K** is E-F-moc-lysine.

Preliminary studies indicate that these preferred analogues possess low hemolytic activity.

In accordance with another embodiment, there are provided derivatives of Magainin I or Magainin II (carboxy- or amide-terminated), preferably Magainin II, wherein a portion of the basic peptide is deleted and at least one of the remaining amino acid residues is substituted as hereinabove described; in particular, amino acid residue 19 is omitted and in addition either amino acid residues 1–4 or 3,5, and 6 are omitted. Preferred peptides are as follows:

FLHSAKKFGKAFVFIMNS
GIKHSAKKFAKAFKAIMNS
FLKSAKKFGKAFVGIMNS
FLKSAKKFAKAFVGIMNS

In accordance with another aspect of the present invention, there is provided a peptide which is a deletion analogue of an amide or carboxy terminated Magainin I, wherein Magainin I is represented by the following structural formula using the single letter amino acid code and the numbers below each amino acid residue refer to the position of the residue in the peptide:

G I G K F L H S A G K F G
1 2 3 4 5 6 7 8 9 10 11 12 13

K A F V G E I M K S
14 15 16 17 18 19 20 21 22 23 and wherein each amino acid residue is a D-amino acid residue or a glycine residue, and at least one of amino acid residues 15 through 23 is omitted. In a preferred embodiment, at least one of amino acid residues 15, 16, 18, 19, 21, 22 and 23 is omitted. In one embodiment, at least amino acid residue 18 is omitted whereas in another embodiment, at least amino acid residue 19 is omitted, and in yet another embodiment at least amino acid residue 21 is omitted. In preferred embodiments, only one of amino acid residues 18, 19, and 21, respectively, is omitted. In other preferred embodiments, amino acid residues 21, 22, and 23 are omitted, amino acid residues 19 through 23 are omitted, amino acid residues 18 through 23 are omitted, and amino acid residues 17 through 23 are omitted. The compound can be a deletion analogue of amide—or carboxy-terminated Magainin I.

In accordance with another aspect of the present invention, there is provided a peptide which is a deletion analogue of an amide—or carboxy-terminated Magainin II, wherein Magainin II is represented by the following structural formula using the single letter amino acid code and the numbers below each amino acid residue refer to the position of the residue in the peptide:

G I G K F L H S A K K F G
1 2 3 4 5 6 7 8 9 10 11 12 13

K A F V G E I M N S
14 15 16 17 18 19 20 21 22 23, wherein each amino acid residue is a D-amino acid residue or a glycine residue, and at least one of amino acids 15 through 22 is omitted. In a preferred embodiment, at least one of amino acids 15, 18, 19, 20, 21, and 22 is omitted. In one embodiment, at least amino acid 18 is omitted. In another embodiment, at least amino acid 19 is omitted. Another embodiment omits at least amino acid 21, and yet other embodiment omits at least amino acid 22. In preferred embodiments, only one of amino acids 18, 19, 21, and 22, respectively, is omitted. The compound can be a deletion analogue of amide-terminated Magainin II.

In accordance with yet another aspect of the present invention, there is provided a basic (positively charged) polypeptide having at least sixteen amino acids wherein the polypeptide includes at least eight hydrophobic amino acids and at least eight hydrophilic amino acids. Each of the amino acid residues of the polypeptide is a D-amino acid residue or a glycine residue. Still more particularly, the hydrophobic amino acids are in groups of two adjacent amino acids wherein the amino acids are D-amino acids or glycine, and each group of two hydrophobic amino acids is spaced from another group of two hydrophobic amino acids by at least one D-amino acid other than a hydrophobic amino acid (preferably at least two D-amino acids) and generally by no greater than four D-amino acids, and the D-amino acids between pairs of hydrophobic amino acids may or may not be hydrophilic.

The hydrophilic amino acids are generally also in groups of two adjacent D-amino acids in which at least one of the two D-amino acids is a basic hydrophilic amino acid, with such groups of two hydrophilic D-amino acids being spaced from each other by at least one amino acid, other than a hydrophilic D-amino acid, wherein each of said at least one amino acid(s) is a D-amino acid or glycine (preferably at least two amino acids) and generally no greater than four amino acids, and the amino acids between pairs of hydrophilic D-amino acids may or may not be hydrophobic.

In accordance with a particularly preferred embodiment, the polypeptide comprises a chain of at least four groups of amino acids wherein each amino acid is a D-amino acid or glycine, with each group consisting of four amino acids wherein each of the at least four amino acids is a D-amino acid or glycine. Two of the four amino acids in each group are hydrophobic amino acids, and two of the four amino acids in each group are hydrophilic, with at least one of the hydrophilic amino acids in each group being a basic hydrophilic amino acid and the other being a basic or neutral hydrophilic amino acid.

The hydrophobic amino acids may be selected from the class consisting of D-Ala, D-Cys, D-Phe, D-Ile, D-Leu, D-Met, D-Val, D-Trp, D-Tyr, and Gly. The neutral hydrophilic D-amino acids may be selected from the class consisting of D-Ser, D-Asn, D-Gln, and D-Thr. The basic hydrophilic D-amino acids may be selected from the class consisting of D-Lys, D-Arg, and D-His, D-ornithine (D-Orn), D-homoarginine (D-Har), D-2,4-diaminobutyric acid (D-Dbu), and D-p-aminophenylalanine.

Each of the groups of four amino acids may be of the sequence ABCD, BCDA, CDAB, or DABC, wherein A and B are each hydrophobic amino acids and may be the same or different, one of C or D is a basic hydrophilic amino acid, and the other of C or D is a basic or neutral hydrophilic amino acid and may be the same or different. In a preferred embodiment, the polypeptide chain may comprise 5 or 6 groups of this sequence. In each group, each of A, B, C and D may be the same in some or all of the groups or may be different in some or all of the groups.

The polypeptide chain preferably has at least 20 amino acids, and no greater than 50 amino acids wherein each amino acid is a D-amino acid or glycine. It is to be understood, however, that the polypeptide does not have to consist entirely of the groups described above. The polypeptide may have amino acids extending from either or both ends of the noted groups forming the polypeptide chain and/or there may be amino acids between one or more of the at least four groups and still remain within the scope of the invention, provided that each amino acid residue of the polypeptide chain is a D-amino acid residue or glycine.

The groups of amino acids may be repeating groups of amino acids, or the amino acids in the various groups may vary provided that in each group of the at least four groups of amino acids there are two hydrophobic amino acids wherein each amino acid is a D-amino acid or glycine, and two hydrophilic D-amino acids as hereinabove noted.

Thus, in a preferred embodiment, the biologically active polypeptide comprises a chain including at least four groups of amino acids, each containing four amino acids wherein each amino acid is a D-amino acid or glycine. Two of the four amino acids in each group are hydrophobic, wherein each hydrophobic amino acid is a D-amino acid or glycine, at least one amino acid is a basic hydrophilic D-amino acid, and the remaining one is a basic or neutral hydrophilic D-amino acid, with the polypeptide chain preferably having at least 20 amino acids but no greater than 50 amino acids.

In one embodiment, each of the at least four groups of amino acids which are in the peptide chain is of the sequence A-B-C-D, B-C-D-A, C-D-A-B or D-A-B-C wherein A and B are hydrophobic, one of C or D is basic hydrophilic, and the other of C or D is basic or neutral hydrophilic. The resulting polypeptide chain, therefore, may have one of the following sequences:

$(X_1)_a(A\text{-}B\text{-}C\text{-}D)_n(Y_1)_b$ $(X_2)(B\text{-}C\text{-}D\text{-}A)_n(Y_2)_b$ $(X_3)_a(C\text{-}D\text{-}A\text{-}B)_n(Y_3)_b$ $(X_4)_a(D\text{-}A\text{-}B\text{-}C)_n(Y_4)_b$ wherein $X_1$ is D; C-D- or B-C-D-, $Y_1$ is -A or -A--B or -A-B-C $X_2$ is A-, D-A- or C-D-A-

$Y_2$ is -B, -B-C or B-C-D $X_3$ is B-, A-B-, D-A-B-

$Y_3$ is -C, -C-D, -C-D-A $X_4$ is C-, B-C-, A-B-C-

$Y_4$ is -D, -D-A, -D-A-B a is 0 or 1; b is 0 or 1 and n is at least 4.

It is to be understood that the peptide chain may include D-amino acids or glycine between the hereinabove noted groups of four amino acids provided that the spacing between such groups and the charge on the D-amino acids or glycine does not change the characteristics of the peptide chain which provide amphiphilicity and a positive charge and do not adversely affect the folding characteristics of the chain to that which is significantly different from one in which the hereinabove noted groups of four amino acids are not spaced from each other.

As representative examples, there may be mentioned.

| | |
|---|---|
| I | D-Ala-D-Phe-D-Ser-D-Lys-D-Ala-D-Phe-D-Ser-D-Lys-D-Ala-D-Phe-D-Ser-D-Lys-D-Ala-D-Phe-D-Ser-D-Lys-D-Ala-D-Phe-D-Ser-D-Lys |
| II | D-Ala-D-Phe-D-Ser-D-Lys-D-Ala-D-Phe-D-Ser-D-Lys-D-Ala-D-Phe-D-Ser-D-Lys-D-Ala-D-Phe-D-Ser-D-Lys-D-Ala-D-Phe-D-Ser-D-Lys-D-Ala-D-Phe-D-Ser-D-Lys. |
| III | D-Phe-D-Ser-D-Lys-D-Ala-D-Phe-D-Ser-D-Lys-D-Ala-D-Phe-D-Ser-D-Lys-D-Ala-D-Phe-D-Ser-D-Lys-D-Ala- |
| IV | D-Ser-D-Lys-D-Ala-D-Phe-D-Ser-D-Lys-D-Ala-D-Phe-D-Ser-D-Lys-D-Ala-D-Phe-D-Ser-D-Lys-D-Ala-D-Phe-D-Ser-D-Lys-D-Ala-D-Phe- |
| V | D-Lys-D-Ala-D-Phe-D-Ser-D-Lys-D-Ala-D-Phe-D-Ser-D-Lys-D-Ala-D-Phe-D-Ser-D-Lys-D-Ala-D-Phe-D-Ser |

The peptide may have amino acids extending from either end of the chain. For example, the chains may have a D-Ser-D-Lys sequence before the "D-Ala" end, and/or a D-Ala-D-Phe sequence after the "D-Lys" end. Other amino acid sequences may also be attached to the "D-Ala" and/or the "D-Lys" end.

Similarly, in any polypeptide chain of the present invention having at least four groups of amino acids of the sequence as described above, the chain may have, for example, a C-D sequence before the first A-B-C-D group. Also other acid sequences including D-amino acids or glycine may be attached to the "A" and/or the "D" end of one of these polypeptide chains. Also there may be D-amino acids or glycine residues in the chain which space one or more groups of the hereinabove noted four amino acids from each other.

Such polypeptides are generally water-soluble to a concentration of at least 20 mg/ml at neutral pH in water. Such polypeptides are non-hemolytic, i.e., they will not rupture red blood cells at effective antimicrobial concentrations. The structure of such polypeptides provides for flexibility of the polypeptide molecule. When the polypeptide is placed in water, it does not assume an amphiphilic structure. When the polypeptide encounters an oily surface or membrane, the polypeptide chain folds upon itself into a rod like structure.

In accordance with a further aspect of the present invention, there is provided a peptide (polypeptide) having from eight to fifteen amino acids comprised of at least four hydrophobic amino acids and four hydrophilic amino acids. Each amino acid residue is a D-amino acid residue or glycine. The hydrophobic amino acids are in groups of two adjacent hydrophobic D-amino acids or glycine wherein each group of two hydrophobic D-amino acids or glycine is spaced from each other by at least one D-amino acid other than a hydrophobic D-amino acid or glycine (preferably at least two D-amino acids) and generally no greater than four D-amino acids, and the D-amino acid(s) between pairs of hydrophobic amino acids wherein each amino acid is a D-amino acid or glycine, may or may not be hydrophilic. The hydrophilic D-amino acids are generally also in groups of two adjacent D-amino acids in which at least one of the two D-amino acids is a basic hydrophilic D-amino acid and the other of the two is basic or neutral. The groups of two hydrophilic D-amino acids are spaced from each other by at least one amino acid other than a hydrophilic D-amino acid, and wherein the at least one amino acid is a D-amino acid or glycine (preferably at least two amino acids) and generally no greater than 4 amino acids, and the amino acids between pairs of hydrophilic amino acids may or may not be hydrophobic.

The peptide having from 8 to 15 amino acids is amphiphilic and is positively charged (basic).

The 8 to 15 amino acid peptide hereinabove described may or may not be bioactive, and in the case where such peptide is not bioactive, it has utility as an intermediate in providing the hereinabove noted peptides which have at least 16 amino acids and which are bioactive. For example, two peptides, one having eight D-amino acids and the other having twelve D-amino acids may be coupled to each other to form a peptide having 20 D-amino acids of the type hereinabove described and which is bioactive. The peptides may be coupled by standard peptide chemistry techniques. Thus, for example, such peptides may be condensed in solution by the technique disclosed by Johnson, et al. Peptides, pages 239–42 (Walter de Gruzter & Co., 1986).

As representative examples of such peptides, there may be mentioned peptides represented by the following structure wherein A, B, C and D are as defined previously;

(i) $(W_1)_a(A-B-C-D)_n(Z_1)_b$
(ii) $(W_2)_a(B-C-D-A)_n(Z_2)_b$
(iii) $(W_3)_a(C-D-A-B)_n(Z_3)_b$
(IV) $(W_4)_a(D-A-B-C)_n(Z_4)_b$ wherein $W_1$ is D-, C-D-, B-C-D-
$W_2$ is A-, D-A-, C-D-A-
$W_3$ is B-, A-B-, D-A-B-
$W_4$ is C-, B-C-, A-B-C-
$Z_1$ is -A, -A-B, -A-B-C
$Z_2$ is -B, -B-C, -B-C-D
$Z_3$ is -C, -C-D, -C-D-A
$Z_4$ is -D, -D-A, -D-A-B n is 2 or 3, a is 0 or 1 and b is 0 or 1.

In accordance with yet another aspect of the present invention, there is provided a peptide which includes the following basic peptide structure X:

-$R_1$-$R_1$-$R_2$-$R_2$-$R_1$-$R_1$-$R_3$-$R_1$-
-$R_1$-$R_1$-$R_3$-$R_1$-$R_1$-$R_4$-$R_5$-$R_1$- wherein $R_1$ is a hydrophobic amino acid;
$R_2$ is a hydrophobic amino acid or a basic hydrophilic amino acid;
$R_3$ is a basic hydrophilic amino acid;
$R_4$ is a hydrophobic or neutral hydrophilic amino acid;
$R_5$ is a basic or neutral hydrophilic amino acid, and each amino acid residue of said peptide is a D-amino acid residue or glycine.

The hereinabove basic structure is hereinafter symbolically indicated as X. Peptides formed in accordance with this basic structure are commonly referred to as CPF peptides.

The CPF peptides of the present invention may include only the hereinabove noted D-amino acids or glycine or may include additional D-amino acids or glycine residues at the amino and/or carboxyl end or both the amino and carboxyl end. In general, the peptide does not include more than 40 amino acids, wherein each amino acid is a D-amino acid or glycine.

The CPF peptides including the above basic structure preferably have from 1 to 4 additional amino acids at the amino end, wherein each amino acid is a D-amino acid or glycine.

Accordingly, such preferred peptides may be represented by the structural formula:

Y—X— wherein X is the hereinabove described basic peptide structure and Y is
(i) $R_5$-, or
(ii) $R_2$-$R_5$-; or
(iii) $R_1$-$R_2$-$R_5$; or
(iv) $R_2$-$R_1$-$R_2$-$R_5$; preferably Glycine -$R_1$-$R_2$-$R_5$.

wherein $R_1$, $R_2$ and $R_5$ are as previously defined.

The carboxyl end of the basic peptide structure may also have additional amino acids which may range from 1 to 13 additional amino acids.

In a preferred embodiment, the basic structure may have from 1 to 7 additional amino acids at the carboxyl end, which may be represented as follows:

-X -Z wherein
X is the hereinabove defined basic peptide structure and Z is
(i) $R_1$-, or
(ii) $R_1$-$R_1$-; or
(iii) $R_1$-$R_1$-$R_4$; or
(iv) $R_1R_1$-$R_4$-$R_4$; or
(v) $R_1$-$R_1$-$R_4$-$R_4$-$R_6$; or
(vi) $R_1$-$R_1$-$R_4$-$R_4$-$R_6$-D-Gln; or
(vii) $R_1$-$R_1$-$R_4$-$R_4$-$R_6$-D-Gln-D-Gln, wherein $R_1$ and $R_4$ are as previously defined, and R6 is D-proline or a hydrophobic amino acid.

Preferred peptides may be represented by the following structural formula $(Y)_a$-X-$(Z)_b$ wherein X, Y and Z are as previously defined and a is 0 or 1 and b is 0 or 1.

As representative examples of CPF peptides used in the present invention, there may be mentioned peptides represented by the following (single letter amino acid code):

G12S3LG4ALKA5LKIG678LGG9(10)QQ
Where:
1=F, L
2=G, A
3=F, L
4=K, L
5=A, G, T
6=A, T
7=H, N
8=A, M, F, L
9=A, S, T
10=P, L Preferred CPF peptides are of the following sequences:

(1) GFGSFLGLALKAALKIGANALGGAPQQ
(2) GLASFLGKALKAGLKIGAHLLGGAPQQ
(3) GLASLLGKALKAGLKIGTHFLGGAPQQ
(4) GLASLLGKALKATLKIGTHFLGGAPQQ
(5) GFASFLGKALKAALKIGANMLGGTPQQ
(6) GFGSFLGKALKAALKIGANALGGAPQQ
(7) GFGSFLGKALKAALKIGANALGGSPQQ
(8) GFASFLGKALKAALKIGANLLGGTPQQ

In accordance with another aspect of the present invention, there is provided a composition comprising at least one biologically active peptide which includes at least a chain of the following 20 amino acid residues having the following peptide structure $X_{10}$ where $X_{10}$ is:

$-R_{11}-R_{12}-R_{11}-R_{11}-R_{13}-R_{13}-\ R_{11}-R_{11}-R_{12}-R_{11}-R_{11}-R_{15}-R_{14}-R_{11}-R_{12}-R_{13}-$ $-R_{11}-R_{16}-R_{15}-R_{17}$, wherein:

$R_{11}$ is a hydrophobic amino acid;
$R_{12}$ is a basic hydrophilic amino acid;
$R_{13}$ is a hydrophobic or basic: hydrophilic amino acid;
$R_{14}$ is a netural hydrophilic amino acid, or a basic hydrophilic amino acid;
$R_{15}$ is a neutral hydrophilic amino acid; $R_{16}$ is D-proline or a hydrophobic amino acid; and $R_{17}$ is a netural hydrophilic, basic hydrophilic or hydrophobic amino acid. Each of the amino acid residues of the peptide is a D-amino acid residue or glycine. The at least one biologically active peptide which includes the peptide structure $X_{10}$ has at least the hereinabove described twenty amino acid peptide and generally no greater than 35 amino acids, preferably no greater than 30 amino acids. Such peptides are derived from fragments of the human hormone cholecystokinin, or may be derivatives of such fragments.

In one embodiment, the at least one biologically active peptide is of the formula $R_{11}$-$R_{11}$-X-, wherein $R_{11}$ is a hydrophobic amino acid as described above. Most preferably, the biologically active peptide of this embodiment includes a chain of at least the following amino acids:

D-Leucine-D-Leucine-X-.

In another embodiment, the at least one biologically active petpide includes a chain of at least the following amino acids:

$-X-R_{12}-R_{11}-R_{15}-R_{11}-R_{11}-$, wherein $R_{11}R_{12}$, and $R_{15}$ are amino acids of the types hereinabove described.

The peptide may be amide-terminated or carboxy-terminated.

In accordance with another aspect of the present invention, there is provided a biologically active amphiphilic peptide which includes the following basic structure $X_{12}$:

$[R_{21}-R_{22}-R_{22}-R_{23}-R_{21}-R_{22}-R_{22}]_n$, wherein $R_{21}$ is a basic hydrophilic amino acid, $R_{22}$ is a hydrophobic amino acid, $R_{23}$ is a neutral hydrophilic or hydrophobic amino acid, n is from 2 to 5, and each amino acid residue of the peptide is a D-amino acid. residue or glycine.

In accordance with one embodiment, the peptide may include the following structure:

$Y_{12}-X_{12}$, wherein $X_{12}$ is as hereinabove described, and Y is:

(i) $R_{22}$;
(ii) $R_{22}-R_{22}$;
(iii) $R_{21}-R_{22}-R_{22}$;
(iv) $R_{23}-R_{21}-R_{22}\ R_{22}$;
(v) $R_{22}-R_{23}-R_{21}-R_{22}-R_{22}$; or
(vi) $R_{22}-R_{22}-R_{23}-R_{21}-R_{22}-R_{22}$, wherein $R_{21}$, $R_{22}$, and $R_{23}$ are as hereinabove described In accordance with another embodiment, the peptide may include the following structure:

$X_{12}-Z_{12}$, wherein $X_{12}$ is as hereinabove described, and $Z_{12}$ is:

(i) $R_{21}$;
(ii) $R_{21}-R_{22}$;
(iii) $R_{21}-R_{22}-R_{22}$
(iv) $R_{21}-R_{22}-R_{22}-R_{23}$;
(v) $R_{21}\ -R_{22}-R_{22}-R_{23}-R_{21}$; or
(vi) $R_{21}-R_{22}-R_{22}-R_{23}-R_{21}-R_{22}$.

In accordance with yet another embodiment, the peptide may include the following structure:

$(Y_{12})_a-X_{12}-(Z_{12})_b$, wherein Y and Z are as previously defined, a is 0 or 1, and b is 0 or 1.

In a preferred embodiment, n is 3, and most preferably the peptide has the following structure as indicated by the single letter amino acid code:

[KIAGKIA]$_3$.

In another embodiment, n is 3, and the peptide has the following structural formula:

[Lys Ile Ala Gly (p-aminophenylalanine) Ile Ala]$_3$

In another embodiment, n is 2, and the peptide preferably is of the following structure as indicated by the single letter amino acid code:

KIA(KIAGKIA)$_2$KIAG.

In accordance with another aspect of the present invention, there is provided a biologically active amphiphilic peptide which includes the following basic structure $X_{14}$:

$R_{21}-R_{22}-R_{22}-R_{23}-R_{21}-R_{22}-R_{22}-R_{21}-R_{22}-R_{22}-R_{22}-R_{21}-R_{22}-R_{22}$, wherein $R_{21}$, $R_{22}$ and $R_{23}$ are as hereinabove described, and each amino acid residue of the peptide is a D-amino acid residue or glycine.

In accordance with one embodiment, the peptide may include the following structure:

$Y_{14}-X_{14}$, wherein $X_{14}$ is as hereinabove described, and Y14 is:

(i) $R_{22}$;
(ii) $R_{22}-R_{22}$;
(iii) $R_{21}-R_{22}-R_{22}$;
(iv) $R_{23}-R_{21}-R_{22}-R_{22}$;
(v) $R_{22}-R_{23}-R_{21}-R_{22}-R_{22}$;
(vi) $R_{22}-R_{22}-R_{23}-R_{21}-R_{22}-R_{22}$, or
(vii) $R_{21}-R_{22}-R_{22}-R_{23}-R_{21}-R_{22}-R_{22}$, wherein $R_{21}$, $R_{22}$ and $R_{23}$ are as hereinabove described.

In accordance with another embodiment, the peptide may include the following structure:

$X_{14}-Z_{14}$, wherein $X_{14}$ is as hereinabove described and $Z_{14}$ is:

(i) $R_{21}$;
(ii) $R_{21}-R_{22}$;
(iii) $R_{21}-R_{22}-R_{22}$;
(iv) $R_{21}-R_{22}-R_{22}-R_{23}$;
(v) $R_{21}-R_{22}-R_{22}-R_{23}-R_{21}$;
(vi) $R_{21}-R_{22}-R_{22}-R_{23}-R_{21}-R_{22}$; or
(vii) $R_{21}-R_{22}-R_{22}-R_{23}-R_{21}-R_{22}-R_{22}$, wherein $R_{21}$, $R_{22}$ and $R_{23}$ are as hereinabove described.

In accordance with yet another embodiment the peptide may include the following structure:

$(Y_{14})a-X_{14}-(Z_{14})b$, wherein $X_{14}$, $Y_{14}$ and $Z_{14}$ are as previously defined, a is 0 or 1, and b is 0 or 1. In a preferred embodiment, the peptide is of the following structural formula as indicated by the single letter amino acid code:
KLASKAGKIAGKIAKVALKAL.

In another preferred embodiment, the peptide is of the following structural formula as indicated by the single letter amino acid code:
KIAGKIAKIAGOIAKIAGKIA.

In accordance with a further aspect of the present invention, the peptide may include the following basic peptide structure $X_{16}$:

-$R_{31}$-$R_{33}$-$R_{32}$-$R_{31}$-$R_{34}$-$R_{34}$-$R_{31}$-
-$R_{31}$-$R_{34}$-$R_{32}$-$R_{31}$-$R_{31}$-$R_{32}$-$R_{31}$-
-$R_{31}$-$R_{31}$-$R_{32}$- wherein $R_{31}$ is a hydrophobic amino acid, $R_{32}$ is a basic hydrophilic amino acid, $R_{33}$ is a neutral hydrophilic, basic hydrophilic, or hydrophobic amino acid, and $R_{34}$ is a hydrophobic or basic hydrophilic amino acid, and each amino acid residue is a D-amino acid residue or glycine. Preferably, $R_{33}$ is a neutral hydrophilic amino acid.

Such peptides are commonly referred to as PGLa peptides.

The PGLa peptides generally include at least seventeen amino acids and may include as many as forty amino acids. Accordingly, the hereinabove described basic peptide structure for a PGLa peptide may include additional amino acids at the amino end or at the carboxyl end or at both the amino and carboxyl end.

Thus, for example, a PGLa peptide may have the following structure:

-$Y_1$-$X_{16}$ where $X_{16}$ is a previously defined; and Y16 is:
(i) $R_{31}$; or
(ii) $R_{34}$-$R_{31}$ where $R_{31}$ and $R_{34}$ are as previously defined.

For example, a PGLa peptide may also have the following structure:

-X16-$Z_{16}$ where $X_{16}$ is a previously defined; and $Z_{16}$ is:
$Y_{16}$ is
(i) $R_{31}$; or
(ii) $R_{31}$-$R_{31}$
where $R_{31}$ is as previously defined.

A PGLa peptide may also have the following structure:
$(Y_{16})a$-$X_{16}$-$(Z_{16})b$ where $X_{16}$, $Y_{16}$, and $Z_{16}$ are as previously defined, a is 0 or 1 and b is 0 or 1.

In accordance with another embodiment, the peptide may include the following basic peptide structure $X_{18}$:

-$R_{31}$-$R_{33}$-$R_{32}$-$R_{31}$-$R_{34}$-$R_{35}$-$R_{33}$-
$R_{31}$-$R_{34}$-$R_{32}$-$R_{31}$-$R_{31}$-$R_{32}$-
$R_{31}$-$R_{31}$-$R_{31}$-$R_{32}$-$(R_{36})n$-$R_{31}$-, wherein $R_{31}$, $R_{32}$, $R_{33}$, and $R_{34}$ are as previously defined, and $R_{35}$ is glutamine or asparagine or a basic hydrophilic, or hydrophobic amino acid, $R_{36}$ is glutamic acid, aspartic acid, a hydrophobic amino acid or a basic hydrophilic amino acid, and n is 0 or 1. Each amino acid residue is a D-amino acid residue or glycine.

Such peptides are commonly referred to as XPF peptides.

The XPF peptides generally include at least nineteen amino acids and may include up to forty amino acids. Accordingly, the hereinabove described basic peptide structure of XPF may include additional amino acids at the amino and carboxyl ends.

Thus, for example, an XPF peptide may include the following structure:

-$Y_{18}$-$X_{18}$- where $X_{18}$ is as previously defined and $Y_{18}$ is
(i) $R_{31}$ or
(ii) $R_{34}$-$R_{31}$
where $R_{31}$ and $R_{34}$ are as previously defined.

An XPF peptide may include the following structure:
-$X_{18}$-$Z_{18}$- where $X_{18}$ is as previously defined and $Z_{18}$ is
(i) $R_{31}$; or
(ii) $R_{31}$-$R_{35}$; or
(iii) $R_{31}$-$R_{35}$-D-Proline; or
(iv) $R_{31}$-$R_{35}$-D-Proline-$R_{32}$ An XPF peptide may also have the following structure:
$(Y_{18})a$-$X_{18}(Z_{18})b$ where $X_{18}$, $Y_{18}$ and $Z_{18}$ are as previously defined, a is 0 or 1, and b is 0 or 1.

Preferred are XPF or PGLa peptides, which are characterized by the following primary amino acid sequence (single letter amino acid code):

PGLa: GMASKAGAIAGKIAKVALKAL (NH$_2$)
XPF: GWASKIGQTLGKIAKVGLKELIQPK

A review of XPF and PGLa can be found in Hoffmann et al., *EMBO J.* 2:711–714, 1983; Andreu et al., *J.Biochem.* 149:531–535, 1985; Gibson et al. *J. Biol Chem.* 261:5341–5349, 1986; and Giovannini et al, *Biochem J.* 243:113–120, 1987.

In accordance with another aspect of the present invention, there is provided an analogue of a biologically active amphiphilic amide or carboxy-terminated peptide, said peptide being represented by the following structural formula, and wherein the numbers below each amino acid residue refer to the position of the residue in the peptide:

| $R_2$ | $R_1$ | $R_2$ | $R_5$ | $R_2$ | $R_1$ | $R_2$ | $R_2$ | $R_1$ | $R_1$ | $R_3$ | $R_1$ | $R_1$ | $R_1$ | $R_3$ |
|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 |

| $R_1$ | $R_1$ | $R_4$ | $R_5$ | $R_1$ | $R_1$ | $R_1$ | $R_4$ | $R_4$ | $R_1$ | $R_6$ | $R_6$ |
|---|---|---|---|---|---|---|---|---|---|---|---|
| 16 | 17 | 18 | 19 | 20 | 21 | 22 | 23 | 24 | 25 | 26 | 27 |

$R_1$ is a hydrophobic amino acid, $R_2$ is a hydrophobic amino acid or a basic hydrophilic amino acid, $R_3$ is a basic hydrophilic amino acid, $R_4$ is a hydrophobic or neutral hydrophilic amino acid, $R_5$ is a basic hydrophilic or a neutral hydrophilic amino acid, and $R_6$ is a neutral hydrophilic amino acid. Each amino acid residue of the peptide is a D-amino acid residue or a glycine residue. At least one of and no more than seven of amino acid residues 2 through 26 are deleted from the peptide. In one embodiment, one of amino acid residues 2 through 26 is deleted from the peptide.

The hydrophobic amino acids are D-Ala, D-Cys, D-Phe, Gly, D-Ile, D-Leu, D-Met, D-Pro, D-Val, D-Trp, D-Tyr, D-norleucine (D-Nle), D-norvaline (D-Nval), and D-cyclohexylalanine (D-Cha).

The neutral hydrophilic amino acids are D-Asn, D-Gln, D-Ser, and D-Thr.

The basic hydrophilic amino acids are D-Lys, D-Arg, D-His, D-Orn, D-homoarginine (D-Har), D-2,4-diaminobutyric acid (D-Dbu), and D-p-aminophenylalanine.

Such analogues are sometimes hereinafter referred to as "deletion analogues." Representative examples of such deletion analogues comprise the following sequences:

(1) GASFLGKALKAALKIGANLLGGTPQQ
(2) GFSFLGKALKAALKIGANLLGGTPQQ
(3) GFAFLGKALKAALKIGANLLGGTPQQ
(4) GFASLGKALKAALKIGANLLGGTPQQ
(5) GFASFGKALKAALKIGANLLGGTPQQ (6) GFASFLGKALKAALKGANLLGGTPQQ
(7) GFASFLGRALKAALKIANLLGGTPQQ
(8) GFASFLGKALKAALKIGNLLGGTPQQ
(9) GFASFLGKALKAALKIGALLGGTPQQ
(10) GFASFLGKALKAALKIGANLGGTPQQ
(11) GFASFLGKALKAALKIGANLLGTPQQ
(12) GFASFLGKALKAALKIGANLLGGPQQ
(13) GFASFLGKALKAALKIGANLLGGTQQ
(14) GFASFLGKALKAALKIGANLLGGTPQ

In accordance with another aspect of the present invention, there is provided a biologically active amphiphilic peptide having the following structural formula:

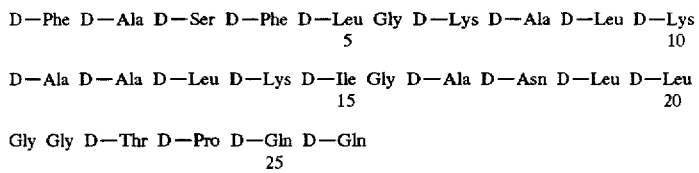

Each amino acid residue which is not a glycine residue is a D-amino acid residue.

In accordance with another aspect of the present invention, there is provided a biologically active amphiphilic peptide which includes the following basic peptide structure $X_{20}$:

$-R_3-R_1-R_2-R_2-R_1-R_1-R_3-R_1-$
$-R_1-R_1-R_3-R_1-R_1-R_4-R_5-R_1-$ wherein $R_1$ is a hydrophobic amino acid;

$R_2$ is a hydrophobic amino acid or a basic hydrophilic amino acid;

$R_3$ is a basic hydrophilic amino acid;

$R_4$ is a hydrophobic or neutral hydrophilic amino acid; and $R_5$ is a basic or neutral hydrophilic amino acid.

Each amino acid residue is a D-amino acid residue or a glycine residue.

The hereinabove basic structure is hereinafter symbolically indicated as $X_{20}$.

The peptide may include only the hereinabove noted amino acids or may include additional amino acids at the amino and/or carboxyl end or both the amino and carboxyl end. In general, the peptide does not include more than 40 amino acids.

The peptides including the above basic structure preferably have from 1 to 4 additional amino acids at the amino end.

Accordingly, such preferred peptides may be represented by the structural formula:

$Y_{20}-X_{20}-$ wherein $X_{20}$ is the hereinabove described basic peptide structure and $Y_{20}$ is:

(i) $R_5$-, or
(ii) $R_2$-$R_5$-; or
(iii) $R_1$-$R_2$-$R_5$; or
(iv) $R_2$-$R_1$-$R_2$-$R_5$; preferably Glycine -$R_1$-$R_2$-$R_5$.

wherein $R_1$, $R_2$ and $R_5$ are as previously defined.

The carboxyl end of the basic peptide structure may also have additional amino acids which may range from 1 to 13 additional amino acids.

In a preferred embodiment, the basic structure may have from 1 to 7 additional amino acids at the carboxyl end, which may be represented as follows:

$-X_{20}-Z_{20}$ wherein $X_{20}$ is the hereinabove defined basic peptide structure and $Z_{20}$ is:

(i) $R_1$-, or
(ii) $R_1$-$R_1$-; or
(iii) $R_1$-$R_1$-$R_4$; or
(iv) $R_1$-$R_1$-$R_4$-$R_4$ or
(v) $R_1$-$R_1$-$R_4$-$R_4$-$R_1$; or
(vi) $R_1$-$R_1$-$R_4$-$R_4$-$R_1$-$R_6$; or
(vii) $R_1$-$R_1$-$R_4$-$R_4$-$R_1$-$R_6$-$R_{61}$ wherein $R_1$ and $R_4$ are as previously defined, and $R_6$ is a neutral hydrophilic amino acid.

Preferred peptides may be represented by the following structural formula $(Y_{20})_a-X_{20}-(Z_{20})_b$ wherein $X_{20}$, $Y_{20}$, and $Z_{20}$ are as previously defined and a is 0 or 1 and b is 0 or 1.

Representative examples of such peptides comprise the following sequences:

(1) GFASKLGKALKAALKIGANLLGGTPQQ; and
(2) GFGSKLGKALKAALKIGANLLGGTPQQ.

In accordance with yet another aspect of the present invention, there is provided a biologically active amphiphilic peptide selected from the class consisting of:

(1) GFGSFLGKALKAALKIGANMLGGSPQQ;
(2) GFGSFLGKALKAALKIGANMLGGSLQQ;
(3) GFGSFLGLALKAALKIGANMLGGAPQQ;
(4) GLASLLGKALKAALKIGANMLGGSPQQ;
(5) GFGSFLGKALKAALKIGANLLGGTPQQ;
(6) GFAKFLGKALKAALKIGANLLGGTPQQ;
(7) GFGKFLGKALKAALKIGANLLGGTPQQ;
(8) GFKKFLGKALKAALKIGANLLGGTPQQ;
(9) GLASFLGKALKAALKIGANLLGGTPQQ; and
(10) GLASLLGKALKAALKIGANLLGGTPQQ.

Each amino acid residue is a D-amino acid residue or a glycine residue.

In accordance with another aspect of the present invention, there is provided a biologically active amphiphilic peptide having the following structural formula:

```
D-Phe D-Ala D-Ser D-Phe D-Leu Gly D-Lys
                        5
D-Ala D-Leu D-Lys D-Ala D-Ala D-Leu D-Lys
                        10
D-Ile Gly D-Ala D-Asn D-Leu D-LeuGly
 15                                  20
Gly D-Thr D-Pro D-Gln D-Gln
                  25
```

Each amino acid residue which is not a glycine residue is a D-amino acid residue.

In accordance with another aspect of the present invention, there is provided a biologically active amphiphilic peptide which includes the following basic structure $X_{22}$:

$R_1-R_2-R_2-R_1-R_2-R_2-R_1-R_1-R_2-R_1-R_1$.

$R_1$ is a hydrophobic amino acid, and $R_2$ is a basic hydrophilic or neutral hydrophilic amino acid.

Each amino acid residue is a D-amino acid residue or a glycine residue.

In one embodiment, the peptide includes the basic structure $Y_{22}-X_{22}$ wherein $X_{22}$ is as hereinabove described and $Y_{22}$ is:

(i) $R_1$;

(ii) $R_2-R_1$; or (iii) $R_2-R_2-R_1$, wherein $R_1$ and $R_2$ are as hereinabove described.

The hydrophobic amino may be selected from the class consisting of D-Ala, D-Cys, D-Phe, Gly, D-Ile, D-Leu, D-Met, D-Pro, D-Val, D-Trp and D-Tyr.

The basic hydrophilic amino acid acids may be selected from the class consisting of D-Lys, D-Arg, D-His, D-Orn, D-homoarginine (D-Har), D-2, 4-diaminobutyric acid (D-Dbu), and D-p-aminophenylalanine. The neutral hydrophilic amino acids may be selected from the class consisting of D-Asn, D-Gln, D-Ser, D-Thr, and D-homoserine (D-Hse).

In one embodiment, $R_1$ is D-leucine. In another embodiment, $R_2$ is D-lysine. Representative examples of peptides in accordance with this aspect of the present invention include those having the following structures:

(1) LKKLKKLLKLL;

(2) LLKKLKKLLKLL;

(3) KLLKKLKKLLKLL; and (4) KKLLKKLKKLLKLL.

In accordance with another aspect of the present invention, there is provided a biologically active amphiphilic peptide which includes the following basic structure $X_{24}$:

$R_2-R_1-R_2-R_2-R_1-R_1-R_2-R_2-R_1-R_2-R_2$ wherein $R_1$ is a hydrophobic amino acid and $R_2$ is a basic hydrophilic or neutral hydrophilic amino acid. Each amino acid residue is a D-amino acid residue or a glycine residue.

In one embodiment, $R_1$ is D-leucine. In another embodiment, $R_2$ is D-lysine.

In one embodiment, the peptide includes the basic structure $Y_{24}-X_{24}$, wherein $X_{24}$ is as hereinabove described, and $Y_{24}$ is:

(i) $R_2$;

(ii) $R_1-R_2$;

(iii) $R_1-R_1-R_2$;

(iv) $R_2-R_1-R_1-R_2$; or (v) $R_2-R_2-R_1-R_1-R_2$.

In one embodiment, the peptide may have the following structure:

D-Lys D-Lys D-Leu D-Leu D-Lys D-Lys D-Leu D-Lys
5
D-Lys D-Leu D-Leu D-Lys D-Lys D-Leu D-Arg D-Arg
10 15

In another embodiment, the peptide includes the basic structure $X_{24}-R_{24}$, wherein $X_{24}$ is as hereinabove described, and $Z_{24}$ is:

(i) $R_1$;

(ii) $R_1-R_1$;

(iii) $R_1-R_1-R_2$;

(iv) $R_1-R_1-R_2-R_2$; or (v) $R_1-R_1-R_2-R_2-R_1$;

In one embodiment, the peptide may have the following structure:

D-Lys D-Leu D-Lys D-Lys D-Leu D-Leu D-Lys D-Lys
5
D-Leu D-Lys D-Lys D-Leu D-Leu D-Lys D-Lys D-Leu
10 15

In another embodiment, the peptide may include the structure:

$(Y_{24})_a - X_{24} - (Z_{24})_b$, wherein $X_{24}$, $Y_{24}$ and $Z_{24}$ are as hereinabove described, and a is 0 or 1, and b is 0 or 1.

In accordance with another aspect of the present invention, there is provided a biologically active amphiphilic peptide which includes the following basic structure $X_{26}$:

$R_1-R_2-R_2-R_1-R_1-R_2-R_2-R_1-R_2-R_2-R_1-R_1-R_2-R_2-R_3$ wherein $R_1$ and $R_2$ are as hereinabove described, and $R_3$ is a neutral hydrophilic amino acid. Each amino acid residue is a D-amino acid residue or a glycine residue.

In one embodiment, the peptide may have the following structure:

LKKLLKKLKKLLKKN

In one embodiment, the peptide may have the following structure:

D-Leu D-Lys D-Lys D-Leu D-Leu D-Lys D-Lys D-Leu D-Lys D-Lys
5 10
D-Leu D-Leu D-Lys D-Lys Xaa, wherein Xaa is D-homoserine.
15

In accordance with yet another aspect of the present invention, there is provided a biologically active amphiphilic peptide which includes the following basic structure $X_{28}$: $R_1-R_2-R_1-R_1-R_2-R_2-R_1-R_1-R_2-R_2-R_4$, wherein $R_1$ and $R_2$ are as hereinabove described, and $R_4$ is a neutral hydrophilic amino acid or proline. Each amino acid residue is a D-amino acid residue or a glycine residue.

In one embodiment, the peptide may include the following structure $Y_{28}-X_{28}$, wherein $X_{28}$ is the basic peptide structure hereinabove described, and $Y_{28}$ is:

(i) $-R_1$;

(ii) $-R_1-R_1$;

(iii) $-R_2-R_1-R_1$;

(iv) $-R_1-R_2-R_1-R_1$;

(v) $-R_1-R_1-R_2-R_1-R_1$;

(vi) $-R_2-R_1-R_1-R_2-R_1-R_1$; or (vii) $-R_2-R_2-R_1-R_1-R_2-R_1-R_1$, wherein $R_1$ and $R_2$ are as hereinabove described.

In one embodiment, the peptide may include the structure: $X_{28}-Z_{28}$, wherein $X_{28}$ is as hereinabove described, and $Z_{28}$ is:

(i) $-R_2$;

(ii) $-R_2-R_2$;

(iii) $-R_2-R_2-R_1$;

(iv) $-R_2-R_2-R_1-R_1$;

(v) $-R_2-R_2-R_1-R_1-R_2$;

(vi) $-R_2-R_2-R_1-R_1-R_2-R_2$; or (vii) $-R_2-R_2-R_1-R_1-R_2-R_1-R_1$.

wherein $R_1$ and $R_2$ are as hereinabove described.

In one embodiment, the peptide may include the structure: $X_{28}-Z_{28}$, wherein $X_{28}$ is as hereinabove described, and $Z_{28}$ is:

(i) $-R_2$;

(ii) $-R_2-R_2$;

(iii) -$R_2$-$R_2$-$R_1$;
(iv) -$R_2$-$R_2$-$R_1$-$R_1$;
(v) -$R_2$-$R_2$-$R_1$-$R_1$-$R_2$;
(vi) -$R_2$-$R_2$-$R_1$-$R_1$-$R_2$-$R_2$; or
(vii) -$R_2$-$R_2$-$R_1$-$R_1$-$R_2$-$R_2$-$R_1$.

In a preferred embodiment, the peptide may have one of the following structures:

(1) LKLLKKLLKKNKKLLKKL; or
(2) LKLLKKLLKKPKKLLKKL.

In another embodiment, the peptide may have the structure $(Y_{28})_a$-$X_{28}$-$(Z_{28})_b$, wherein $X_{28}$, $Y_{28}$ and $Z_{28}$ are as hereinabove described, a is 0 or 1, and b is 0 or 1.

In accordance with another aspect of the present invention, there is provided a biologically active amphiphilic peptide which includes the following basic structure $X_{30}$:

$R_1$-$R_1$-$R_2$-$R_2R_1$-$R_2$-$R_2$-$R_1$-$R_1$-$R_2$-$R_2$-$R_1$-$R_3$, wherein $R_1$, $R_2$ and $R_3$ are as hereinabove described. Each amino acid residue is a D-amino acid residue or a glycine residue.

In accordance with another embodiment, the peptide may include the structure $Y_{30}$-$X_{30}$, wherein $X_{30}$ is as hereinabove described, and $Y_{30}$ is:

(i) -$R_1$;
(ii) -$R_2$-$R_1$;
(iii) -$R_2$-$R_2$-$R_1$;
(iv) -$R_1$-$R_2$-$R_2$-$R_1$;
(v) -$R_1$-$R_1$-$R_2$-$R_2$-$R_1$;
(vi) -$R_2$-$R_1$-$R_1$-$R_2$-$R_2$-$R_1$; or
(vii) -$R_2$-$R_2$-$R_1$-$R_1$-$R_2$-$R_2$-$R_1$, wherein $R_1$ and $R_2$ are as hereinabove described.

In another embodiment, the peptide includes the structure $X_{30}$-$Z_{30}$, wherein $X_{30}$ is as hereinabove described, and $Z_{30}$ is:

(i) -$R_1$;
(ii) -$R_1$-$R_5$;
(iii) -$R_1$-$R_5$-$R_5$;
(iv) -$R_1$-$R_5$-$R_5$-$R_3$;
(v) -$R_1$-$R_5$-$R_5$-$R_3$-$R_1$;
(vi) -$R_1$-$R_5$-$R_5$-$R_3$-$R_1$-$R_3$;
(vii) -$R_1$-$R_5$-$R_5$-$R_3$-$R_1$-$R_3$-$R_3$;
(viii) -$R_1$-$R_5$-$R_5$-$R_3$-$R_1$-$R_3$-$R_3$-$R_5$; or
(ix) -$R_1$-$R_5$-$R_5$-$R_3$-$R_1$-$R_3$-$R_3$-$R_5$-$R_3$, wherein $R_1$ and $R_3$ are as hereinabove described, and $R_5$ is proline.

In one embodiment, the peptide has the following structure:

LLKKLKKLLKKLQGPPQGQSPQ.

In one embodiment, the peptide may have the structure $(Y_{30})_a$-$X_{30}(Z_{30})_b$, wherein $X_{30}$, $Y_{30}$, and $Z_{30}$ are as hereinabove described, a is 0 or 1, and b is 0 or 1.

In accordance with another aspect of the present invention, there is provided a biologically active amphiphilic peptide which includes the following basic structure $X_{32}$:

$R_1$-$R_1$-$R_3$-$R_2$-$R_1$-$R_1$-$R_1$-$R_1$-$R_1$-$R_1$-$R_2$-$R_1$-$R_1$-$R_2$-$R_2$-$R_1$-$R_1$-$R_2$-$R_2$-$R_1$-, wherein $R_1$, $R_2$, and $R_3$ are as hereinabove described. Each amino acid residue is a D-amino acid residue or a glycine residue. In one embodiment, the peptide may have the following structure:

LASKAGAIAGKIAKKLLKKL

In another embodiment, the peptide may include the structure $X_{32}$-$Z_{32}$, wherein $X_{32}$ is as hereinabove described, and $Z_{32}$ is:

(i) -$R_2$;
(ii) -$R_2$-$R_2$;
(iii) -$R_2$-$R_2$-$R_1$;
(iv) -$R_2$-$R_2$-$R_1$-$R_1$;
(v) -$R_2$-$R_2$-$R_1$-$R_2$;
(vi) -$R_2$-$R_2$-$R_1$-$R_1$-$R_2$-$R_2$; or
(vii) -$R_2$-$R_2$-$R_1$-$R_1$-$R_2$-$R_2$-$R_1$.

In accordance with yet another aspect of the present invention, there is provided a biologically active amphiphilic peptide having a structure selected from the group consisting of:

(a) $R_1$-$R_2$-$R_2$-$R_1$-$R_2$-$R_2$-$R_1$;
(b) $R_1$-$R_1$-$R_2$-$R_2$-$R_1$-$R_2$-$R_2$-$R_1$;
(c) $R_2$-$R_1$-$R_1$-$R_2$-$R_2$-$R_1$-$R_2$-$R_2$-$R_1$;
(d) $R_2$-$R_2$-$R_1$-$R_1$-$R_2$-$R_2$-$R_1$-$R_2$-$R_2$-$R_1$; and
(e) $R_1$-$R_2$-$R_2$-$R_1$-$R_1$-$R_2$-$R_2$-$R_1$-$R_2$-$R_2$-$R_1$, wherein $R_1$ and $R_2$ are as hereinabove described.

In one embodiment, the peptide has the structure (a), and a representative example of such a structure is LKKLKKL.

In another embodiment, the peptide has the structure (b), and a representative example of such a structure is LLKKLKKL.

In another embodiment, the peptide has the structure (c), and a representative example of such a structure is KLLKKLKKL.

In yet another embodiment, the peptide has the structure (d), and a representative example of such a structure is KKLLKKLKKL.

In a further embodiment, the peptide has the structure (e), and representative examples of such a structure are LKKLLKKLKKL and AKKLLKKLKKL as given in the accompanying sequence listing.

In accordance with another aspect of the present invention, there is provided a biologically active amphiphilic peptide having the following structural formula:

LKKLLKKLKKLLKR.

Each amino acid residue is a D-amino acid residue.

In accordance with another aspect of the present invention, there is provided a peptide having the following structural formula:

D-Ile $R_1$ D-Lys D-Phe D-Leu D-Lys D-Lys D-Ala D-Lys D-Lys D-Phe
5                                                                          10
D-Gly D-Lys $R_2$ D-Phe $R_3$ D-Lys $R_4$ $R_5$ D-Lys D-Lys,
15                                                    20 wherein $R_1$ is Gly or D-Lys; $R_2$ is D-Ala or D-Lys;

$R_3$ is D-Val or D-Lys; $R_4$ is D-Ile or D-Glu; and $R_5$ is D-Leu or D-Ile. Each amino acid residue which is not a glycine residue is a D-amino acid residue.

In one embodiment, the peptide has the following structural formula:

D-Ile Gly D-Lys D-Phe D-Leu D-Lys D-Lys D-Ala D-Lys D-Lys D-Phe
5                                                                          10
D-Gly D-Lys D-Ala D-Phe D-Val D-Lys D-Ile D-Leu D-Lys D-Lys
15                                                    20

In another embodiment, the peptide has the following structural formula:

D-Ile D-Lys D-Lys D-Phe D-Leu D-Lys D-Lys D-Ala D-Lys D-Lys
                      5                                10
D-Phe Gly D-Lys D-Lys D-Phe D-Lys D-Lys D-Ile D-Leu D-Lys D-Lys.
              15                                 20

In yet another embodiment, the peptide has the following structural formula:

D-Ile Gly D-Lys D-Phe D-Leu D-Lys D-Lys D-Ala D-Lys D-Lys
                     5                              10
D-Phe Gly D-Lys D-Lys D-Phe D-Lys D-Lys D-Glu D-Ile D-Lys D-Lys
              15                                20

In accordance with another aspect of the present invention, there is provided a peptide having the following structural formula:

Gly R₁ Gly D-Lys R₂ D-Leu D-Lys D-Lys D-Ala D-Lys D-Lys
                    5                             10
R₃ Gly D-Lys D-Ala R₄ D-Val D-Lys R₅ D-Leu D-Lys D-Lys,
            15                          20 wherein each of $R_1$, $R_2$, $R_3$, $R_4$ and $R_5$ is D-Ile or D-norleucine. Each amino acid residue which is not a glycine residue is a D-amino acid residue.

In one embodiment, each of $R_1$, $R_2$, $R_3$ $R_4$ and $R_5$ is D-Ile, and such a peptide has the following structural formula:

Gly D-Ile Gly D-Lys D-Ile D-Leu D-Lys D-Lys D-Ala D-Lys
                    5                             10
D-Lys D-Ile Gly D-Lys D-Ala D-Ile D-Val D-Lys D-Ile D-Leu
              15                          20
D-Lys D-Lys

In another embodiment, each of $R_1$, $R_2$, $R_3$, $R_4$ and $R_5$ is D-norleucine, and such a peptide has the following structural formula:

Gly Xaa Gly D-Lys Xaa D-Leu D-Lys D-Lys D-Ala D-Lys
                    5                           10
D-Lys Xaa Gly D-Lys D-Ala Xaa D-Val D-Lys Xaa D-Leu
              15                         20
D-Lys D-Lys, wherein Xaa is D-norleucine.

In accordance with another aspect of the present invention, there is provided a peptide having the following structural formula:

Gly D-Ile Gly D-Lys D-Phe D-Leu D-Lys D-Lys D-Ala D-Lys
                    5                             10
D-Lys D-Phe Gly D-Lys D-Ala D-Phe D-Val D-Lys D-Ile R

D-Lys D-Lys, wherein R is D-Val or D-norleucine. Each amino acid residue which is not a glycine residue is a D-amino acid residue.

In one embodiment, R is D-Val, and the peptide has the following structural formula:

GIGKFLKKAKKFGKAFVKIVKK

In another embodiment, R is D-norleucine and the peptide has the following structural formula:

Gly D-Ile Gly D-Lys D-Phe D-Leu D-Lys D-Lys
                   5
D-Ala D-Lys D-Lys D-Phe Gly D-Lys D-Ala
          10                      15

-continued
D-Phe D-Val D-Lys D-Ile Xaa D-Lys D-Lys,
                  20 wherein Xaa is D-norleucine.

In accordance with yet another aspect of the present invention, there is provided a peptide having the following structural formula:

Gly D-Ile Gly D-Lys D-Phe D-Leu D-Lys D-Lys
                    5
D-Ala D-Lys D-Lys D-Phe Gly D-Lys D-Ala
          10                       15
D-Phe D-Val D-Lys D-Ile D-Leu D-Lys D-Lys R,
                  20 wherein R is D-Arg, D-Asn, or D-homoserine. Each amino acid residue which is not a glycine residue is a D-amino acid residue.

In one embodiment, R is D-Arg, and the peptide has the following structural formula:

GIGKFLKKAKKFGKAFVKILKKR

In another embodiment, R is D-Asn, and the peptide has the following structural formula:

GIGKFLKKAKKFGKAFVKILKKN.

In another embodiment, R is D-homoserine, and the peptide has the following structural formula:

Gly D-Ile Gly D-Lys D-Phe D-Leu D-Lys D-Lys
                    5
D-Ala D-Lys D-Lys D-Phe Gly D-Lys D-Ala
          10                       15
D-Phe D-Val D-Lys D-Ile D-Leu D-Lys D-Lys Xaa,
                  20 wherein Xaa is D-homoserine.

In accordance with another aspect of the present invention, there is provided a peptide including the following structural formula:

—R₁ Gly D-Ile Gly D-Lys D-Phe D-Leu D-Lys D-Lys
                       5
D-Ala D-Lys D-Lys D-Phe Gly D-Lys D-Ala D-Phe
          10                          15
D-Val D-Lys D-Ile D-Leu D-Lys D-Lys-,
              20 wherein $R_1$ is D-Met or D-Arg. Each amino acid residue which is not a glycine residue is a D-amino acid residue.

In one embodiment, $R_1$ is D-Met, and the peptide has the following structural formula:

MGIGKFLKKAKKFGKAFVKILKK

In another embodiment, the peptide includes the following structural formula:

—R₁ R₁ Gly D-Ile Gly D-Lys D-Phe D-Leu D-Lys D-Lys
                         5                            10
D-Ala D-Lys D-Lys D-Phe Gly D-Lys D-Ala
                    15
D-Phe D-Val D-Lys D-Ile D-Leu D-Lys D-Lys-.
                  20

In one embodiment, each $R_1$ is D-Arg, and the peptide has the following structural formula:

RRGIGKFLKKAKKFGKAFVKILKK

In another embodiment, the peptide includes the following structural formula:

—$R_1$ $R_1$ Gly D-Ile Gly D-Lys D-Phe D-Leu D-Lys D-Lys
                  5                                    10
D-Ala D-Lys D-Lys D-Phe Gly D-Lys D-Ala
                                 15
D-Phe D-Val D-Lys D-Ile D-Leu D-Lys D-Lys
                         20
$R_2$—, wherein $R_1$ is D-Met or D-Arg, and $R_2$ is a hydrophobic amino acid.

The hydrophobic amino acids are D-Ala, D-Cys, D-Phe, D-Ile, D-Leu, D-Met, Gly, D-Trp, D-Pro, D-Tyr, D-Val, D-norleucine, and D-norvaline.

In one embodiment, $R_2$ is Gly, and in a preferred embodiment, each $R_1$ is D-Arg, and the peptide has the following structural formula:

RRGIGKFLKKAKKFGKAFVKILKKG

In accordance with another aspect of the present invention, there is provided a peptide including the following structural formula:

Gly D-Ile Gly D-Lys D-Phe D-Leu D-Lys D-Lys
                 5
D-Ala D-Lys D-Lys D-Phe Gly D-Lys D-Ala
         10                              15
D-Phe D-Val D-Lys D-Ile D-Leu D-Lys D-Lys
                        20
$R_1$ $R_2$-.

wherein $R_1$ is D-Asp or D-Ile, and $R_2$ is D-Asp or D-Glu. Each amino acid residue which is not a glycine residue is a D-amino acid residue.

In one embodiment, the peptide includes the following structure.

—Gly D-Ile Gly D-Lys D-Phe D-Leu D-Lys D-Lys
                   5
D-Ala D-Lys D-Lys D-Phe Gly D-Lys D-Ala
         10                              15
D-Phe D-Val D-Lys D-Ile D-Leu D-Lys D-Lys
                        20
$R_1$ $R_2$ $R_3$,
          25 wherein $R_3$ is a hydrophobic amino acid or a basic hydrophilic amino acid.

The basic hydrophilic amino acids are D-Lys, D-Arg, D-His, D-ornithine (D-Orn), D-homoarginine (D-Har), D-2,4-diaminobutyric acid (D-Dbu), and D-p-aminophenylalanine.

In one embodiment, the peptide has the following structural formula:

GIGKFLKKAKKFGKAFVKILKKDDK

In another embodiment, the peptide includes the following structure:

—Gly D-Ile Gly D-Lys D-Phe D-Leu D-Lys D-Lys
                   5
D-Ala D-Lys D-Lys D-Phe Gly D-Lys D-Ala D-Phe
         10                              15
D-Val D-Lys D-Ile D-Leu D-Lys D-Lys $R_1$ $R_2$ $R_3$
                        20
$R_4$-.

wherein $R_4$ is a basic hydrophilic amino acid.

In one embodiment, the peptide has the following structural formula:

GIGKFLKKAKKFGKAFVKILKKIEGR

In accordance with another aspect of the present invention, there is provided a peptide selected from the group consisting of:

(1) GIIGKFLKKAKKFGKAFVKILKK;

(2) GIGKFLKLAKKFGKAFVKILKK;

(3) GIGKFLKKAKKGIGAVLKVLTTGK;

(4) GIGKFLKKAKKFGKAFIKILKK;

(5) GIGKFLKKAKKFG(Har)AFVKILKK;

(6) GIGKFLKKAKKFGKAFVKILKK;

(7) GGKFLKKAKKFGKAFVKILKK; and (8) FGKILKKAKKIGKAIVKFLKK.

Each amino acid residue which is not a glycine residue is a D-amino acid residue.

In accordance with another aspect of the present invention, there is provided a biologically active amphiphilic peptide having the following structural formula $X_{34}$:

$R_1$-$R_1$-$R_2$-$R_1$-$R_1$-$R_2$-$R_2$-$R_1$-$R_1$-$R_2$-$R_2$-$R_1$-$R_2$-$R_2$, wherein $R_1$ is a hydrophobic amino acid, and $R_2$ is a basic hydrophilic or neutral hydrophilic amino acid. Each amino acid residue which is not a glycine residue is a D-amino acid residue.

The hydrophobic amino acids are selected from the group consisting of D-Ala, D-Cys, D-Phe, Gly, D-Ile, D-Leu, D-Met, D-methionine sulfoxide, D-Val, D-Trp, and D-Tyr.

The basic hydrophilic amino acids are selected from the group consisting of D-Lys, D-Arg, D-His, D-Orn, D-homoarginine (D-Har), D-2,4-diaminobutyric acid (Dbu), and D-p-aminophenylalanine.

The neutral hydrophilic amino acids are selected from the group consisting of D-Asn, D-Gln, D-Ser, and D-Thr.

In accordance with one embodiment, $R_1$ is D-leucine. In accordance with another embodiment, $R_2$ is D-lysine.

In a preferred embodiment, the peptide has the following structure (I):

I.

D—LeuD—LeuD—LysD—LeuD—LeuD—LysD—LysD—LeuD—LeuD—LysD—LysD—LeuD—LysD—Lys
                           5                                                           10

In accordance with another aspect of the present invention, there is provided a biologically active amphiphilic peptide having the following structural formula $X_{36}$:

$R_2$-$R_1$-$R_1$-$R_2$-$R_2$-$R_1$-$R_2$-$R_2$-$R_1$-$R_1$-$R_2$-$R_2$-$R_1$-$R_1$, wherein $R_1$ and $R_2$ are as hereinabove described. Each amino acid residue which is not a glycine residue is a D-amino acid residue.

In a preferred embodiment, the peptide has the following structure (II):

II.

D—LysD—LeuD—LeuD—LysD—LysD—LeuD—LysD—LysD—LeuD—LeuD—LysD—LysD—LeuD—Leu
                            5                                        10

In accordance with yet another aspect of the present invention, there is provided a biologically active amphiphilic peptide having the following structural formula $X_{38}$:

$R_1$-$R_2$-$R_1$-$R_1$-$R_2$-$R_2$-$R_1$-$R_1$-$R_2$-$R_2$-$R_1$-$R_2$-$R_2$-$R_1$-$R_1$-$R_2$-$R_2$-$R_1$, wherein $R_1$ is a hydrophobic amino acid, and $R_2$ is a basic hydrophilic or neutral hydrophilic amino acid as before defined. Each amino acid residue which is not a glycine residue is a D-amino acid residue.

Preferably, the peptide has the following structure (III):

D—LeuD—LysD—LeuD—LeuD—LysD—LysD—LeuD—LeuD—LysD—LysD—LeuD—LysD—Lys
                            5                                    10

D—LeuD—LeuD—LysD—LysD—Leu
            15

In accordance with another aspect of the present invention, there is provided a compound comprising an analogue of Peptide III, said peptide being in an amide-or carboxy-terminated (preferably amide-terminated) form. The Peptide III, also hereinafter sometimes referred to as the "parent peptide," is represented by the following structural formula, and the numbers below each amino acid residue refer to the position of the residue in the peptide.

D—LeuD—LysD—LeuD—LeuD—LysD—LysD—LeuD—LeuD—LysD—LysD—LeuD—LysD—Lys
  1      2     3    4     5     6     7    8     9    10    11    12   13

D—LeuD—LeuD—LysD—LysD—Leu
 14   15    16    17   18

The parent peptide is substituted in at least one of positions 1, 3, 4 and 7–18 as follows:

| Residue No. | Substituent |
| --- | --- |
| 1 | D-Methionine sulfoxide, D-Lys, or D-Met |
| 3 | D-Methionine sulfoxide, D-Lys, or D-Met |
| 4 | D-Methionine sulfoxide, D-Lys, D-Met, D-His, D-Ser, or D-Arg |
| 7 | D-Methionine sulfoxide, D-Lys, or D-Met |
| 8 | D-Methionine sulfoxide, D-Lys, or D-Met |
| 9 | D-Methionine sulfoxide |
| 10 | D-Methionine sulfoxide |
| 11 | D-Methionine sulfoxide, D-Met, D-Ser, D-Lys, D-Arg, D-His or Gly |
| 12 | D-Methionine sulfoxide |
| 13 | D-Methionine sulfoxide, or D-Met |
| 14 | D-Methionine sulfoxide, D-Lys, or D-Met |
| 15 | D-Methionine sulfoxide, D-Lys, or D-Met |
| 16 | D-Methionine sulfoxide |
| 17 | D-Methionine sulfoxide |
| 18 | D-Methionine sulfoxide, or D-Met |

Each amino acid residue which is not a glycine residue is a D-amino acid residue.

In accordance with one embodiment, at least one of amino acid residues, 1, 7, 8, 11, 14, 15, and 18 can be substituted with D-methionine sulfoxide.

In accordance with another embodiment, at least one of amino acid residues 1, 7, 8, 14, 15, and 18 can be substituted with a D-methionine residue.

In accordance with yet another embodiment, at least one of amino acid residues 4, 7, 8, 11, and 14 can be substituted with a D-lysine residue.

In accordance with a further embodiment, amino acid residue 4 is substituted with a D-lysine residue, and amino acid residue 11 is substituted with a D-methionine residue.

In accordance with another embodiment, at least one of amino acid residues 4 and 11 can be substituted with a D-arginine residue.

In accordance with yet another embodiment, at least one of amino acid residues 4 and 11 can be substituted with a D-histidine residue.

In accordance with another embodiment, amino acid residue 11 is substituted with a glycine residue.

In accordance with another aspect of the present invention, there is provided a compound comprising an analogue of the parent peptide hereinabove described, said peptide being in an amide- or carboxy-terminated (preferably amide-terminated) form, wherein at least one of the amino acid residues 1 through 7, 9, 11, 12, 14, 16 or 18 is deleted from the parent peptide. Each amino acid residue is a D-amino acid residue. In one embodiment, at least one of amino acid residues 3, 7, 11, 14, or 18 is deleted from the parent peptide. In other embodiments, amino acid residues 1 through 3, 1 through 4, 1 through 5, 1 through 6, and 1 through 7 are deleted from the peptide.

Representative examples of such peptides include the following:

(1) D–Leu D–Leu D–Lys D–Lys D–Leu D–Lys D–Lys D–Leu
                        5

D–Leu D–Lys D–Lys D–Leu
          10

(2) D–Lys D–Lys D–Leu D–Leu D–Lys D–Lys D–Leu D–Lys D–Lys
                        5

D–Leu D–Leu D–Lys D–Lys D–Leu
          10

In accordance with a further aspect of the present invention, there is provided a biologically active amphiphilic peptide which includes the following structural formula $X_{40}$:

$R_1$-$R_1$-$R_2$-$R_2$-$R_1$-$R_2$-$R_2$-$R_1$-$R_1$-$R_2$-$R_2$-$R_1$-$R_1$, wherein $R_1$ and $R_2$ are as hereinabove described. Each amino acid residue which is not a glycine residue is a D-amino acid residue.

In one embodiment, the peptide can include the following structure:

$X_{40}$-$Z_{40}$, wherein $X_{40}$ is as hereinabove described, and $Z_{40}$ is:
(i) $R_2$;
(ii) $R_2$-$R_1$; or
(iii) $R_2$-$R_1$-$R_1$.

In one embodiment, the peptide has the following structural formula:

D—LeuD—LeuD—LysD—LysD—LeuD—LysD—LysD—LeuD—LeuD—LysD—LysD—Leu
            5                                    10

D—LeuD—LysD—LeuD—Leu
         15

Figure 1:
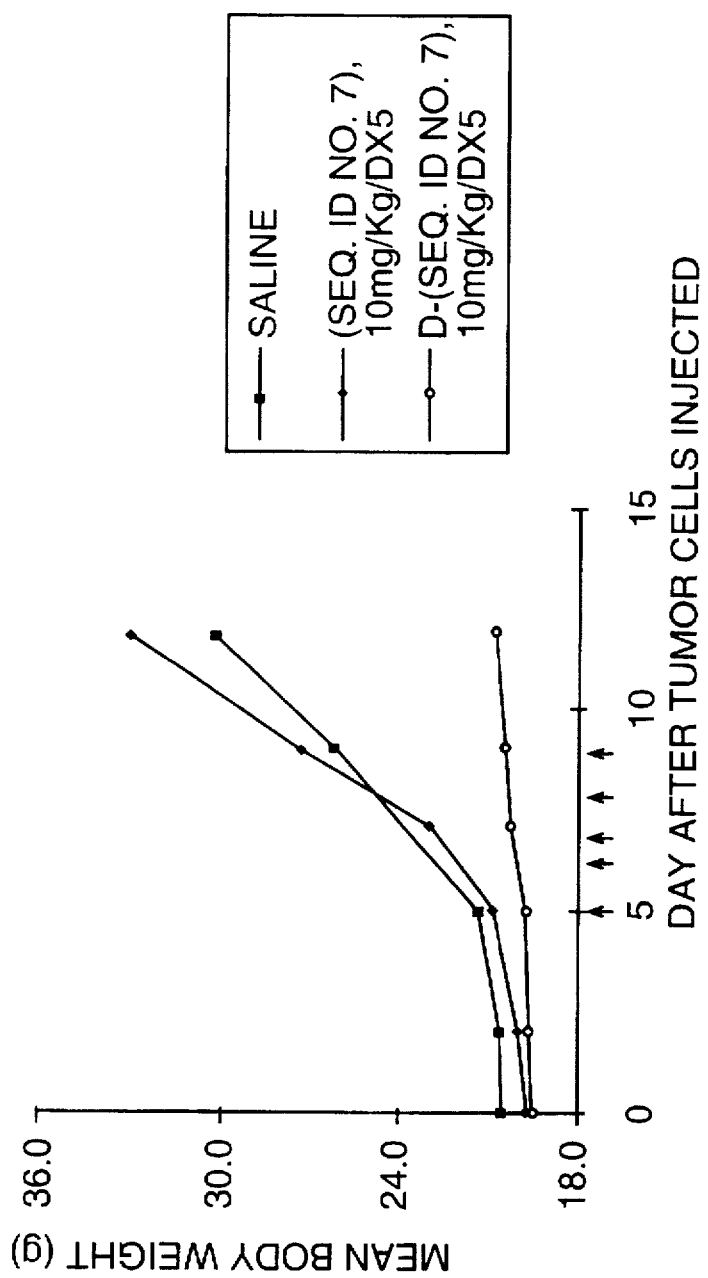
FIG. 1 demonstrates that administration of a D-amino acid peptide delayed and reduced the accumulation of ascites in mice compared to controls after injection of Spontaneous Ovarian Teratoma cells.

Applicants unexpectedly have found that the above-mentioned peptides, all of which consist entirely of D-amino acids or glycine residues, have biological activity.

The above-mentioned peptides also have increased resistance to proteolytic enzymes while retaining their biological activity. Therefore, such peptides may be administered orally.

In general the peptides hereinabove described are ion channel-forming peptides. Thus, in accordance with an aspect of the present invention, there is provided a biologically active amphiphilic peptide or protein. The peptide or protein is an ion channel-forming peptide or protein. At least one amino acid residue of the peptide or protein is optically active, and each optically active amino acid residue is a D-amino acid residue.

The term "optically active" as used herein means that the amino acid residue may exist in the D-form or the L-form. It is to be noted, however, that glycine is not optically active; however, glycine may be included in the peptide or protein if all other amino acid residues in the peptide or protein are D-amino acid residues.

An ion channel-forming peptide or protein or ionophore is a peptide or protein which increases the permeability of ions across a natural or synthetic lipid membrane. B. Christensen, et al., *PNAS*, Vol. 85, pgs. 5072–5076 (July 1988) describes methodology which indicates whether or not a peptide has ion channel-forming properties and is therefore an ionophore. As used herein, an ion channel-forming peptide or ion channel-forming protein is a peptide or protein which has ion channel-forming properties as determined by the method of Christensen, et al.

An amphiphilic peptide or protein is a peptide or protein which includes both hydrophobic and hydrophilic regions.

In general, the peptides hereinabove described, and/or analogues or derivatives thereof are generally water soluble to a concentration of at least 20 mg/ml at neutral pH in water. In addition, such peptides are non-hemolytic; i.e., they will not rupture blood cells at effective concentrations. The peptides cause less than 5% hemolysis of human erythrocytes at a concentration of 500 µg/ml. In addition, the structure of such peptide provides for flexibility of the peptide molecule. When the peptide is placed in water, it does not assume an amphiphilic structure. When the peptide encounters an oily surface or membrane, the peptide chain folds upon itself into a rod-like structure.

The peptides may be C-terminal acids or amides.

The peptides may be administered to a host; for example a human or non-human animal, in an amount effective to inhibit growth of a target cell or virus. Thus, for example, the peptides and/or analogues or derivatives thereof may be used as antimicrobial agents, anti-viral agents, antibiotics, anti-tumor agents, antiparasitic agents, spermicides, as well as exhibiting other bioactive functions.

The term "antimicrobial" as used herein means that the peptides of the present invention inhibit, prevent, or destroy the growth or proliferation of microbes such as bacteria, fungi, or the like.

The term "antibiotic" as used herein means that the peptides employed in the present invention produce effects adverse to the normal biological functions of the cell, tissue, or organism including death or destruction and prevention of the growth or proliferation of the biological system when contacted with the peptides.

The term "spermicidal" as used herein means that the peptides employed in the present invention, inhibit, prevent, or destroy the motility of sperm.

The term "antiviral" as used herein means that the peptides employed in the present invention inhibit, prevent, or destroy the growth or proliferation of viruses.

The term "anti-tumor" as used herein means that the peptide inhibits the growth of or destroys tumors.

The term "antiparasitic" as used herein means that the peptides of the present invention may be used to inhibit the growth of or destroy parasites.

The peptides of the present invention have a broad range of potent antibiotic activity against a plurality of microorganisms including Gram-positive and Gram-negative bacteria, fungi, protozoa, and the like, as well as parasites. The peptides of the present invention allow a method for treating or controlling microbial infection caused by organisms which are sensitive to the peptides. Such treatment may comprise administering to a host organism or tissue susceptible to or affiliated with a microbial infection an antimicrobial amount of at least one of the peptides.

Because of the antibiotic properties of the peptides, they may also be used as preservatives or sterilants of materials susceptible to microbial contamination.

The peptide may be administered in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptide compositions may also be used in combination with adjuvants, protease inhibitors, or compatible drugs where such a combination is seen to be desirable or advantageous in controlling infection caused by harmful microorganisms including protozoa, viruses, and the like, as well as by parasites.

The peptides of the present invention may be administered to a host; in particular an animal, in an effective antibiotic and/or anti-tumor and/or anti-viral and/or antimicrobial and/or anti-parasitic and/or an antispermicidal amount.

Depending on the use, a composition in accordance with the invention will contain an effective anti-microbial amount and/or an effective antispermicidal amount and/or an effective anti-viral amount and/or an effective anti-tumor amount and/or an effective antibiotic amount and/or anti-parasitic amount of one or more of the hereinabove described peptides which have such activity.

The peptide of the present invention may also be employed in promoting or stimulating healing of a wound in a host.

The term "wound healing" as used herein includes various aspects of the would healing process.

These aspects include, but are not limited to, increased contraction of the wound, increased deposition of connective tissue, as evidenced by, for example, increased deposition of collagen in the wound, and increased tensile strength of the wound, i.e., the peptides increase wound breaking strength. The peptides of the present invention may also be employed so as to prevent the inhibition of wound healing in individuals having a compromised immune system.

The peptides of the present invention may be used in the treatment of external burns and to treat and/or prevent skin and burn infections. In particular, the peptides may be used to treat skin and burn infections caused by organisms such as, but i not limited to, P. aeruginosa and S. aureus.

The peptides are also useful in the prevention or treatment of eye infections. Such infections may be caused by bacteria such as, but not limited to, P. aerurinosa, S. aureus and N. gonorrhoeae, by fungi such as but not limited to C. albicans and A. fumigatus, by parasites such as but not limited to A. castellani, or by viruses.

The peptides may also be effective in killing cysts, spores, or trophozoites of infection-causing organisms. Such organisms include, but are not limited to Acanthamoeba which forms trophozoites or cysts, C. albicans, which forms spores, and A. fumigatus, which forms spores as well.

In general, the peptide is employed to provide peptide dosages of from 0.1 mg. to 500 mg. per kilogram of host weight. When administered topically, the peptide is used in a concentration of from 0.05% to 10%.

The peptides may be produced by known techniques and obtained in substantially pure form. For example, the peptides may be synthesized on an automatic synthesizer. *Journal of the American Chemical Society*, Vol. 85, pgs. 2149–54 (1963). It is also possible to produce such peptides by genetic engineering techniques.

The peptides of the present invention may be administered alone, or in combination with other such peptides. The peptides may also be administered in combination with biologically active peptides or proteins containing L-amino acid residues, such as ion channel-forming proteins, or the peptides of the present invention may be administered in combination with other active components, such as ions having pharmacological properties or antibiotics.

Biologically active peptides containing L-amino acid residues which may be administered in combination with the peptides of the present invention include magainin peptides, PGLa peptides, XPF peptides, cecropins, and sarcotoxins. Magainin peptides are described in *Proc. Natl. Acad. Sci.*, Vol. 84, pgs 5449–53 (August 1987). A review of XPF and PGLa peptides may be found in Hoffman, et al., *EMBOJ.*, 2:711–714 (1983). Andreu, et al., *J. Biochem*, 149:531–535 (1985); Gibson, et al., *Biochem J.*, 243:113–120 (1987).

The cecropins and analogues and derivatives thereof are described in *Ann. Rev. Microbiol.*, Vol. 41, pgs, 103–26 (1987), and Christensen, et al., *PNAS*, Vol. 85, pgs. 5072–5076, (1988). Sarcotoxins and analogues and derivatives thereof are described in Molecular Entomotogy, pgs 369–78, Alan R. Liss, Inc. (1987).

Ion channel-forming proteins or peptides which may be employed in combination with the peptides of the present invention include defensins, also known as human neutrophil antimicrobial peptides (HNP), major basic protein (MBP) of eosinophils, bactericidal permeabil.ity-increasing protein (BPI), and a pore-forming cytotoxin called variously perforin, cytolysin, or pore-forming protein. Defensins are described in Selsted, et al., *J. Clin. Invest.*, Vol. 76, pgs. 1436–1439 (1985). MBP proteins are described in Wasmoen, et al., *J. Biol. Chem.*, Vol. 263, pgs. 12559–12563 (1988). BPI proteins are described in Ooi, et al., *J. Biol. Chem.* Vol. 262, pgs. 14891–14894 (1987). Perforin is described in Henkart, et al., *J. Exp. Med.*, 160:75 (1984), and in Podack, et al., *J. Exp. Med.*, 160:695 (1984). The above articles are hereby incorporated by reference.

Ions having pharmacological properties which may be employed in combination with the peptides of the present invention include anions such as fluoride, peroxide, and bicarbonate anions, and cations such as silver, zinc, mercury, arsenic, copper, platinum, antimony, gold, thallium, nickel, selenium, bismuth, and cadmium cations.

A ion having pharmacological properties is one which when introduced into a target cell inhibits and/or prevents and/or destroys the growth of the target cell.

Such an ion having pharmacological properties is one which in the absence of an ion channel forming peptide is unable to cross a natural or synthetic lipid membrane; in particular a cell membrane, in sufficient amounts to affect a cell adversely.

The peptide and the ion having pharmacological properties, whether administered or prepared in a single composition or in separate compositions, are employed in amounts effective to inhibit and/or prevent and/or destroy the growth of the target cell. In effect, the ion potentiates the action of the peptide, i.e., the amount of ion is effective to reduce the maximum effective concentration of the peptide or protein for inhibiting growth of a target cell.

Antibiotics which may be employed in combination with the peptides of the present invention include bacitracins, aminoglycosides, hydrophobic antibiotics, including macrolide antibiotics, penicillins, monobactams, or derivatives or analogues thereof.

Other antibiotics which may be used (whether or not hydrophobic) in combination with the peptides of the present invention are antibiotics which are 50-S ribosome inhibitors such as lincomycin; clindamycin; and chloramphenicol; etc.; and antibiotics which have a large lipid like lactone ring, such as mystatin; pimaricin, etc.

The peptide and antibiotic may be administered by direct administration to a target cell or by systemic or topical administration to a host which includes the target cell, in order to prevent, destroy or inhibit the growth of a target cell. Target cells whose growth may be prevented, inhibited, or destroyed by the administration of the peptides and antibiotic include Gram-positive and Gram-negative bacteria as well as fungal cells.

The antibiotic, such as those hereinabove described, or derivatives or analogues thereof, when used topically, is generally employed in a concentration of about 0.1% to about 10%. When used systemically, the antibiotic or derivative or analogue thereof is generally employed in an amount of from 1.25 mg. to about 45 mg. per kg. of host weight per day. Peptide dosages may be those as hereinabove described.

As representative examples of administering the peptide and antibiotic for topical or local administration, the peptide could be administered in an amount of from about 0.1% to about 10% weight to weight, and the antibiotic is delivered in an amount of from about 0.1% to about 10% weight to weight.

In accordance with another embodiment, the peptides of the present invention may be administered in combination with an antiparasitic agent or an antifungal agent.

Antiparasitic agents which may be employed include, but are not limited to, anti-protozoan agents. Examples of specific anti-parasitic agents which may be employed include, but are not limited to, pentamidine isethionate, and propamidine isethionate (Brolene).

Anti-fungal agents which may be employed include, but are not limited to, ketoconazole. It is also to be understood that certain anti-parasitic agents may also have anti-fungal activity, and that certain anti-fungal agents may have antiparasitic activity.

In accordance with another embodiment, the peptides of the present invention may be administered in combination with an antibiotic which inhibits DNA gyrase, which is an enzyme involved in the formation of bonds between individual coiling strands of replicating bacterial DNA. Thus, DNA gyrase is necessary for the normal replication of bacterial DNA, and, therefore, antibiotics which inhibit DNA gyrase inhibit the normal replication of bacterial DNA.

Examples of antibiotics which inhibit DNA gyrase include nalidixic acid, oxolinic acid, cinoxacin, and quinolone antibiotics which include ciprofloxacin, norfloxacin, ofloxacin, enoxacin, pefloxacin, lomefloxacin, fleroxacin, tosulfloxacin, temafloxacin, and rufloxacin.

In accordance with another embodiment, the peptides of the present invention may be administered for the purpose hereinabove described in combination with other biologically active amphiphilic peptides, or in combination with ion channel-forming proteins.

The invention will now be further described with respect to the following examples; however, the scope of the present invention is not to be limited thereby.

In the following examples, the term "D" indicates that each amino acid residue is a D-amino acid residue or a glycine residue, and the term "Oct" indicates that the peptide is substituted at the N-terminal with an octanoyl group.

EXAMPLE 1

The procedure for the following antibacterial assay is based upon the guidelines of the National Committee for Clinical Laboratory Standards, Document M7-T2, Volume 8, No. 8, 1988.

Stock solutions of the following peptides:
(SEQ ID NO:1)-NH$_2$
D-(SEQ ID NO:1)-NH$_2$
(SEQ ID NO:2)-NH$_2$
D-(SEQ ID NO:2)-NH$_2$
(SEQ ID NO:3)-NH$_2$
D-(SEQ ID NO:3)-NH$_2$
(SEQ ID NO:4)-NH$_2$
D-(SEQ ID NO:4)-NH$_2$
(SEQ ID NO:5)-NH$_2$
D-(SEQ ID NO:5)-NH$_2$
(SEQ ID NO:6)-NH$_2$
D-(SEQ ID NO:6)-NH$_2$
(SEQ ID NO:7)-NH$_2$
D-(SEQ ID NO:7)-NH$_2$
(SEQ ID NO:8)-NH$_2$
D-(SEQ ID NO:8)-NH$_2$
(SEQ ID NO:9)-NH$_2$
D-(SEQ ID NO:9)-NH$_2$
(SEQ ID NO:10)-NH$_2$
D-(SEQ ID NO:10)-NH$_2$
Oct-(SEQ ID NO:11)-NH$_2$
Oct-D-(SEQ ID NO:11)-NH$_2$ were prepared at a concentration of 512 µpg/ml in sterile deionized distilled water and stored at −70° C. The "D" indicates that each amino acid residue of the peptide is a D-amino acid residue or a glycine residue.

The stock peptide solutions are diluted in serial dilutions (1:2) down the wells of a microtiter plate so that the final concentrations of peptides in the wells are 0.25, 0.50, 1, 2, 4, 8, 16, 32, 64, 128, and 256 µg/ml. $1.5 \times 10^5$ CFUs/ml of either S. aureus ATCC 25923, E. coli ATCC 25922, P. aeruginosa ATCC 27853, or C. albicans were added to the wells in full strength Mueller Hinton broth (BBL 11443) from a mid-log culture. The inoculums are standarized spectrophotometrically at 600 nm and is verified by colony counts. The plates are incubated for 16–20hours at 37° C., and the minimal inhibitory concentration (MIC) for each peptide is determined. Minimal inhibitory concentration is defined as the lowest concentration of peptide which produces a clear well in the microtiter plate. The MIC values for each peptide are given in Table I below:

TABLE I

| | MIC (µg/ml) | | | |
|---|---|---|---|---|
| Peptide | S. aureus | P. aeruginosa | E. coli | C. albicans |
| (SEQ ID NO:1)-NH$_2$ | 8 | 16 | 4 | N/A |
| D-(SEQ ID NO:1)-NH$_2$ | 8 | 32 | 4 | N/A |
| (SEQ ID NO:2)-NH$_2$ | 4 | 2 | 4 | 64 |
| D-(SEQ ID NO:2)-NH$_2$ | 4 | 4 | 4 | 32 |
| (SEQ ID NO:3)-NH$_2$ | 8 | 8 | 4 | 32 |
| D-(SEQ ID NO:3)-NH$_2$ | 8 | 4 | 2 | N/A |
| (SEQ ID NO:4)-NH$_2$ | 4 | 4 | 4 | N/A |
| D-(SEQ ID NO:4)-NH$_2$ | 8 | 8 | 4 | 32 |
| (SEQ ID NO:5)-NH$_2$ | 16 | 32 | 4 | N/A |
| D-(SEQ ID NO:5)-NH$_2$ | 32 | 32 | 4 | 32 |
| (SEQ ID NO:6)-NH$_2$ | 4 | 8 | 2 | 32 |
| D-(SEQ ID NO:6)-NH$_2$ | 4 | 8 | 2 | 16 |
| (SEQ ID NO:7)-NH$_2$ | 4 | 4 | 2 | 64 |
| D-(SEQ ID NO:7)-NH$_2$ | 4 | 4 | 2 | 16 |
| (SEQ ID NO:8)-NH$_2$ | 32 | >256 | 256 | 256 |
| D-(SEQ ID NO:8)-NH$_2$ | 16 | >256 | >256 | 256 |
| (SEQ ID NO:9)-NH$_2$ | 16 | 8 | 32 | 32 |
| D-(SEQ ID NO:9)-NH$_2$ | 32 | 8 | 32 | 32 |
| (SEQ ID NO:10)-NH$_2$ | 16 | 8 | 8 | 32 |
| D-(SEQ ID NO:10)-NH$_2$ | 8 | 8 | 16 | 32 |
| Oct-(SEQ ID NO:11)-NH$_2$ | 4 | 4 | 8 | 32 |
| Oct-D-(SEQ ID NO:11)-NH$_2$ | 4 | 4 | 8 | 32 |

The above results indicate that when all residues of the biologically active peptide are D-amino acid residues or glycine residues, the peptides retain their biological activity.

EXAMPLE 2

50 µl of prereduced brain-heart infusion broth (BHI broth) is added to each well of a 96-well microtiter plate. Stock solutions of (SEQ ID NO:8)-NH$_2$ and D-(SEQ ID NO:8)-

$NH_2$ are diluted in serial dilutions (1:2) down the wells of a microtiter plate so that the final concentrations of the peptides in the wells are 0.25, 0.50, 1, 2, 4, 8, 16, 32, 64, 128, and 256 μg/ml. Prereduced saline, vancomycin, and metronidazole are used as controls in the same concentrations. Following the serial dilutions of the antimicrobial agents and the peptides, 100μl of prereduced BHI broth is added to every well and the plate is incubated overnight in an anaerobic chamber. Inoculums of *C. difficile*, *B. fragilis*, *L. fermentum*, and *E. coli* were obtained from overnight cultures in BHI under anaerobic conditions. A 1:100 dilution of the overnight cultures were made in prereduced saline; 0.5 ml of the 1:100 dilution of each of the overnight cultures then was added to 9.5 ml saline to create concentrations of approximately $10^5$ organisms per ml. 50 μl of the cell suspensions then were added to each well. One row of wells serves as a control, and receives no organisms; another row of wells receives only cells without antimicrobial agents or peptides. The plates are incubated anaerobically for 24 to 36 hours, and then visual endpoints are read either as "positive " or "negative." The minimum inhibitory concentration (MIC) is the concentration where no turbidity is observed. The MIC values for each peptide against each organism are given in Table II below.

TABLE II

| | MIC (μg/ml) | | | |
|---|---|---|---|---|
| Peptide | *C. difficile* | *B. fragilis* | *L. fermentum* | *E. coli* |
| (SEQ ID NO:8)-$NH_2$ | 1 | 2 | 8 | 256 |
| D-(SEQ ID NO:8)-$NH_2$ | 1 | 1 | 1 | >256 |

EXAMPLE 3

Stock cultures of P.gingivalis strains 381; A7AI-28; FAY-19M-1; and W-50 are maintained on Brucella blood agar plates with hemin and vitamin $K_1$ (BBL, Cockeysville, Md.), grown under anaerobic conditions (Coy Anaerobic Chambers, Ann Arbor, Mich.) with an atmosphere of 80% $N_2$, 10% $H_2$, and 10% $CO_2$ at 37° C. The cultures then are grown up in brain heart infusion broth (BHI broth) (BBL, Cockeysville, Md.), plus hemin (2.5 mg/1) (Sigma Chemical Co., St. Louis, Mo.) plus 0.25 mg/l vitamin $K_1$ (Sigma Chemical Co.). For antimicrobial susceptibility testing, cultures are taken from overnight (24 hour) broth cultures and diluted in fresh BHI broth (plus hemin and vitamin $K_1$) to deliver $1 \times 10^6$ colony forming units (CFU's) per ml in each microtiter test well.

Antimicrobial susceptibility testing is performed according to the guidelines of the National Committee for Clinical Laboratory Standards, Document M11-T2 (1989). Microtiter plates (Corning, Corning, N.Y.) are aseptically filled with BHI broth (plus hemin and vitamin $K_1$) to a volume of 100μl with a Beckman Biomek 1000 robotic instrument (Beckman Instruments, Palo Alto, Calif.). Peptides (SEQ ID NO:1)-$NH_2$, D-(SEQ ID NO:1)-$NH_2$, (SEQ ID NO:6)-$NH_2$, D-(SEQ ID NO:6)-$NH_2$, (SEQ ID NO:7)-$NH_2$, and D-(SEQ ID NO:7)-$NH_2$, are tested in duplicate lanes by adding manually 100μl of a 1.024 mg/ml peptide solution in water (wt./vol.) to the top wells of a microtiter plate. The peptide is serially diluted 1:2 by mixing and transferring 100 μl from the top well down to the bottom well in the lane with the Beckman Biomek 1000. The last 100 μl from the bottom well is discarded. 100μl of bacteria is added in BHI broth (plus hemin and vitamin $K_1$) to each test well to give final peptide concentrations of 256 μg/ml, 128 μg/ml, 64 μg/ml, 32 μg/ml, 16 μg/ml, 8 μg/ml, 4 μg/ml, 2 μg/ml, 1 μg/ml, 0.50 μg/ml, and 0.25 μg/ml. The plates are incubated in an anaerobic chamber at 37° C. for 24 to 48 hours. After incubation, the minimum inhibitory concentration (MIC) is determined as the lowest concentration of peptide which inhibits growth as determined by visual inspection and optical density when read on a Dynatech MR5000 (Dynatech Laboratories, Chantilly, Va.) microtiter plate reader at 630 nm. The MIC values for each peptide against the various *P. gingivalis* strains are given in Table III below.

TABLE III

| | MIC (μg/ml) *P. gingivalis* strain | | | |
|---|---|---|---|---|
| Peptide | 381 | A7AI-28 | FAY-19M-1 | W-50 |
| (SEQ ID NO:1)-$NH_2$ | 256 | 64 | 64 | 32 |
| D-(SEQ ID NO:1)-$NH_2$ | 256 | 32 | 64 | 8 |
| (SEQ ID NO:6)-$NH_2$ | 64 | 64 | 128 | 256 |
| D-(SEQ ID NO:6)-$NH_2$ | 2 | 8 | 8 | 8 |
| (SEQ ID NO:7)-$NH_2$ | 256 | 2 | 32 | 8 |
| D-(SEQ ID NO:7)-$NH_2$ | 32 | 2 | 8 | 2 |

EXAMPLE 4

Melanoma cell lines WM-239-A (metastatic melanoma), WM278 (primary melanoma), WM793 (primary melanoma) and WM1158 (metastatic melanoma) were seeded in 24-well plates at a concentration of $7.5 \times 10^4$ cells/ml containing 2% tumor medium.

Peptides (SEQ ID NO:6) and D-(SEQ ID NO:6), in which each amino acid residue is a D-amino residue or a glycine residue, were frozen at −20° C. in 100 ml aliquots at a concentration of 25 mg/ml. Each peptide was then dissolved in sterile distilled water at a dilution of 1:1,000 or 1:5,000 to provide peptide concentrations of 25 μg/ml or 5 μg/ml, respectively. The peptides at the 25 μg/ml or 5 μg/ml concentrations were then added to the plates containing the melanoma cells. The amount of $^3$H-thymidine incorporation for each well was taken on days 1, 3, and 7. The percentage of growth reduction of each cell line after 7 days by each peptide is given in Table IV below.

TABLE IV

| | Dose | % Growth Reduction (7 days) | | | |
|---|---|---|---|---|---|
| Peptide | (μg/ml) | WM239-A | WM-278 | WM793 | WM1158 |
| (SEQ ID NO:6) | 5 | 0 | 0 | 11.6 | 0 |
| | 25 | 95.8 | 96.0 | 98.0 | 98.5 |
| D-(SEQ ID NO:6) | 5 | 82.0 | 93.1 | 95.6 | 98.0 |
| | 25 | 96.3 | 96.1 | 98.4 | 98.8 |

EXAMPLE 5

Peptides (SEQ ID NO:10) and D-(SEQ ID NO:10), in which each amino acid is a D-amino acid residue, are tested for % growth reduction of melanoma cell lines WM852 (grown in 2% tumor media or PF media), WM983A (grown in 2% tumor media or PF media), WM793 (grown in 2% tumor media), and WM1985 (grown in PF media) according to the procedure of Example 4, except that only a concentration of 25 µg/ml was employed for (SEQ ID NO:10), and concentrations of 1.0, 2.5, 5.0, 10.0, and 25.0 µg/ml were employed for D-(SEQ ID NO:10). The results are given in Table V below.

WM164
WM902B
WM793; and
WM239A.

The following day, the media are removed, and solutions of peptides D-(SEQ ID NO:6) and D-(SEQ ID NO:10) in 2% tumor media are added in triplicate at the following concentrations:

0 (control)

TABLE V

| Peptide | Dose (µg/ml) | % Growth Reduction (7 days) | | | | | |
|---|---|---|---|---|---|---|---|
| | | WM852-2% | WM-983A-2% | WM793-2% | WM852-PF | WM983A-PF | WM1985-PF |
| (SEQ ID NO:10) | 25 | 0 | 0 | 8.3 | 54.0 | 60.5 | 43.0 |
| D-(SEQ ID NO:10) | 1.0 | 3.0 | 0 | N/A | 2.9 | 3.3 | 5.5 |
| | 2.5 | 5.4 | 0 | 18.2 | 22.9 | 13.9 | 23.6 |
| | 5.0 | 8.8 | 0 | 0 | 32.4 | 29.8 | 52.1 |
| | 10.0 | 16.2 | 13.8 | 12.3 | 80.6 | 84.9 | 84.3 |
| | 25.0 | 84.7 | 71.3 | 84.9 | 91.1 | 90.0 | 92.6 |

EXAMPLE 6

The following melanoma cell lines are seeded in 200 ul of 2.0% tumor medium at a density of $1.5 \times 10^4$ cells per well in a 96-well microtiter plate:

WM1791A
WM35
WM852
WM983A
WM1366
WM8
WM115
WM983B
WM39
WM1158
SKMel 23

1.0 µg/ml
5.0 µg/ml
25.0 µg/ml

On the next day, 1 µCi of 3H-thymidine is added to each well. After 18 hours, the medium was discarded, and the cells were detached by addition of 50 ul of trypsin/versene solution. The loose cells were then harvested using a Tomtec cell harvester. The cells were trapped on filters, and the radioactivity quantitated by liquid scintillation counting using a Packard instrument. The radioactive counts for each cell line contacted with the peptides is given in Table VI below.

TABLE VI

| Peptide | Dose µg/ml | Radioactive Counts | | | | | | |
|---|---|---|---|---|---|---|---|---|
| | | WM1791A | WM35 | WM852 | WM983A | WM1366 | WM115 | WM983B |
| D-(SEQ ID NO:6) | 0 | 8068 | 74761 | 198000 | 389000 | 307000 | 296000 | 202000 |
| | 1 | 5655 | 47241 | 169000 | 335000 | 288000 | 222000 | 225000 |
| | 5 | 1065 | 3187 | 2699 | 5598 | 1910 | 373 | 135 |
| | 25 | 456 | 360 | 554 | 313 | 1692 | 263 | 115 |
| D-(SEQ ID NO:10) | 0 | 9359 | 76294 | 191000 | 300000 | 303000 | 298000 | 211000 |
| | 1 | 6188 | 44803 | 163000 | 217000 | 366000 | 213000 | 195000 |
| | 5 | 3318 | 8779 | 109180 | 49809 | 327000 | 37989 | 45654 |
| | 25 | 642 | 333 | 1083 | 304 | 787 | 424 | 104 |

| Peptide | Dose µg/ml | Radioactive Counts | | | | | | | |
|---|---|---|---|---|---|---|---|---|---|
| | | WM39 | WM8 | WM1158 | SkMe123 | WM164 | WM902B | WM973 | WM239A |
| D-(SEQ ID NO:6) | 0 | 27768 | 17189 | 159000 | 142000 | 153000 | 54570 | 88754 | 37986 |
| | 1 | 27635 | 19226 | 131000 | 114846 | 158000 | 49299 | 81675 | 38053 |
| | 5 | 1308 | 248 | 884 | 2028 | 4143 | 150 | 7284 | 221 |
| | 25 | 273 | 99 | 2108 | 429 | 331 | 75 | 770 | 459 |
| D-(SEQ ID NO:10) | 0 | 27887 | 19099 | 144000 | 141000 | 142000 | 55940 | 88816 | 42505 |
| | 1 | 31033 | 21340 | 130000 | 114000 | 162000 | 47809 | 94365 | 33359 |
| | 5 | 13760 | 3320 | 135000 | 64253 | 17235 | 23390 | 87751 | 8649 |
| | 25 | 199 | 13 | 4949 | 377 | 182 | 72 | 257 | 15 |

EXAMPLE 7

Groups of mice, with 5 or 6 mice in each group, were injected with Spontaneous Ovarian Teratoma Cells. At 2 days and 5 days after the injection of the Spontaneous Ovarian Teratoma Cells (SOT cells), the groups of mice were injected intraperitoneally with a control saline solution, adriamycin, or with one of the following peptides:

(SEQ ID NO:6)-NH$_2$
D-(SEQ ID NO:6)-NH$_2$
(SEQ ID NO:7)-NH$_2$
D-(SEQ ID NO:7)-NH$_2$

The mice in each group were then monitored for median survival time (in days) and for increase in life span (ILS) vis-a-vis the control group. The median survival time is the day of death of the third mouse in each group. The result for the groups of mice given intraperitoneal injections of peptide at days 2 and 5 following injection of SOT cells are given in Table VII below.

TABLE VII

| Peptide | Dose (mg/kg/day) | Median Survival Time (days) | ILS |
|---|---|---|---|
| (SEQ ID NO:6)-NH$_2$ | 60/50 | >42(21) | 100% |
| D-(SEQ ID NO:6)-NH$_2$ | 45 | 38(21) | 83% |
| D-(SEQ ID NO:6)-NH$_2$ | 15 | 35(21) | 67% |
| (SEQ ID NO:7)-NH$_2$ | 22 | 38(21) | 81% |
| D-(SEQ ID NO:7)-NH$_2$ | 22 | 41.5(17) | 144% |

In other experiments the mice are not treated with peptide (SEQ ID NO:7)-NH$_2$ or D-(SEQ ID NO:7)-NH$_2$ in an amount of 10 mg/kg until day five after injection of the Spontaneous Ovarian Teratoma Cells. As shown in FIG. 1, the body weight data indicates that the accumulation of ascites fluid in mice treated with D-(SEQ ID NO:7)-NH$_2$ was delayed and was also significantly less than the control group which was given a saline solution or for animals treated with (SEQ ID NO:7)-NH$_2$.

The peptides of the present invention, whether administered alone or in combination with agents such as toxic ions, antibiotics, or other biologically active peptides or proteins as hereinabove described, may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule or the like. The peptide and/or agent as hereinabove described may also be used in combination with adjuvants, protease inhibitors, or compatible drugs where such a combination is seen to be desirable or advantageous in controlling infection caused by harmful microorganisms including protozoa, viruses, and the like.

The peptide may be administered to a host, in particular an animal, in an effective antibiotic and/or anti-tumor and/or antiviral and/or antimicrobial and/or antispermicidal and/or antiparasitic amount, or in an amount effective to stimulate wound healing in a host. The peptides may be administered either alone or in combination with an ion having pharmacological properties, antibiotic, or ion channel-forming peptide or protein as hereinabove described. When the peptide is administered in combination with an ion having pharmacological properties, the activity of the peptide is potentiated.

When the peptide is administered in combination with an agent as hereinabove described, it is possible to administer the peptide and agent in separate forms. For example, the agent may be administered systemically and the peptide may be administered topically.

When the peptide is administered topically, it may be administered in combination with a water-soluble vehicle, said water-soluble vehicle being in the form of an ointment, cream, lotion, paste or the like. Examples of water-soluble vehicles which may be employed include, but are not limited to, glycols, such as polyethylene glycol, hydroxycellulose, and KY Jelly. The water-soluble vehicle is preferably free of an oily substance.

The peptide may also be employed alone, or in combination with other peptides of the present invention, or in combination with peptides containing L-amino acid residues, or in combination with other active components (eg., ions having pharmacological properties, antibiotics) as hereinabove described in the form of an oral composition for oral hygiene. Such a composition may be incorporated into a wide variety of compositions and materials used for oral hygiene purposes, which include, but are not limited to, toothpastes, mouthwashes, tooth gels, and tooth powders. Such composition may thus be used to treat or prevent periodontal disease, to prevent or reduce plaque, and/or to prevent or treat or reduce dental caries. The peptide may be used to inhibit, prevent, or destroy the growth of *Streptococcus mutans*, which is associated with dental caries and periodontal disease.

Numerous modifications and variations of the present invention are possible in light of the above teachings and, therefore, within the scope of the accompanying claims, the invention may be practiced other than as particularly described.

What is claimed is:

1. A biologically active amphiphilic compound comprising:
    a peptide analog of Magainin I peptide or Magainin II peptide,
        said Magainin I peptide or Magainin II peptide analog being in an amide-or carboxy-terminated form,
    wherein Magainin I is represented by the following structural formula using the single letter amino acid code and the numbers below each amino acid residue refer to the position of the residue in the peptide:

G I G K F L H S A G K F G
1 2 3 4 5 6 7 8 9 10 11 12 13

K A F V G E I M K S
          14 15 16 17 18 19 20 21 22 23 wherein each amino acid residue which is not a glycine residue is a D-amino acid residue, and
    wherein Magainin II is represented by the following structural formula using the single letter amino acid code and the numbers below each amino acid residue refer to the position of the residue in the peptide:

G I G K F L H S A K K F G
1 2 3 4 5 6 7 8 9 10 11 12 13

K A F V G E I M N S
          14 15 16 17 18 19 20 21 22 23, wherein each amino acid residue which is not a glycine residue is a D-amino acid residue, and
    wherein said peptide analog is obtained by deleting the amino acid residue in position 19 and substituting at least one of amino acid residues 3, 7, 8, 10, 13, 15, 16, 18, 21, 22, or 23 with another amino acid as follows:

| Residue Number | Substituent |
| --- | --- |
| 3 | D-Leu |
| 7 | D-Lys |
| 8 | D-Lys, D-Ala |
| 10 | D-Ala, D-Lys |
| 13 | D-Trp, D-Leu, D-Phe, D-Ala |
| 15 | D-Phe |
| 16 | D-Ala |
| 18 | D-Lys, D-Ala, D-Phe |
| 21 | D-Lys, D-Ile, D-Leu |
| 22 | D-Lys |
| 23 | D-Lys, D-Ser, D-Asn. |

2. The compound of claim 1, wherein the analog is an analog of Magainin II selected from the group consisting of:

D-(SEQ ID No.2);

D-(SEQ ID NO.3);

D-(SEQ ID NO.4);

D-(SEQ ID NO.6); and

D-(SEQ ID No.7).

3. A composition comprising the compound of claim 1 and a carrier.

4. A biologically active amphiphilic peptide
    which is a peptide analog of Magainin I peptide or Magainin II peptide,
        said Magainin I peptide or Magainin II peptide analog being in an amide-or carboxy-terminated form, and
    wherein Magainin I is represented by the following structural formula using the single letter amino acid code and the numbers below each amino acid residue refer to the position of the residue in the peptide:

```
G I G K F L H S A G K F G K A F V G E I M K S
1 2 3 4 5 6 7 8 9 10 11 12 13 14 15 16 17 18 19 20 21 22 23
``` wherein each amino acid residue which is not a glycine residue is a D-amino acid residue, and wherein Magainin II is represented by the following structural formula using the single letter amino acid code and the numbers below each amino acid residue refer to the position of the residue in the peptide:

```
G I G K F L H S A K K F G K A F V G E I M N S
1 2 3 4 5 6 7 8 9 10 11 12 13 14 15 16 17 18 19 20 21 22 23,
``` wherein each amino acid residue which is not a glycine residue is a D-amino acid residue, and wherein said peptide analog is obtained by deleting the amino acid residue in position 19 and substituting at least one of amino acid residues 3, 7, 8, 10, 13, 15, 16, 18, 21, 22, or 23 with another amino acid as follows:

| Residue Number | Substituent |
| --- | --- |
| 3 | D-Leu |
| 7 | D-Lys |
| 8 | D-Lys, D-Ala |
| 10 | D-Ala, D-Lys |
| 13 | D-Trp, D-Leu, D-Phe, D-Ala |
| 15 | D-Phe |
| 16 | D-Ala |
| 18 | D-Lys, D-Ala, D-Phe |
| 21 | D-Lys, D-Ile, D-Leu |
| 22 | D-Lys |
| 23 | D-Lys, D-Ser, D-Asn. |

5. A composition comprising the compound of claim 4 and a carrier.

6. A pharmaceutical composition comprising the compound of claim 4 and an acceptable pharmaceutical carrier.

7. A process for treating a microbial infection in a host, comprising the step of administering to the host an antimicrobially effective amount of the peptide of claim 4.

8. A process for treating a tumor in a mammalian host, comprising the step of administering to the host an antitumor effective amount of the peptide of claim 4.

* * * * *

UNITED STATES PATENT AND TRADEMARK OFFICE
CERTIFICATE OF CORRECTION

PATENT NO.: 5,792,831

DATED: August 11, 1998

INVENTOR(S): W. Lee MALOY

It is certified that an error appears in the above-identified patent and that said Letters Patent is hereby corrected as shown below:

In Claim 2, Col. 44, line 47, "No." should read --NO.--.

In Claim 2, Col. 44, line 54, "No." should read --NO.--.

Signed and Sealed this

Twenty-fourth Day of November, 1998

Attest:

BRUCE LEHMAN

Attesting Officer　　　　Commissioner of Patents and Trademarks

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

Lys Ile Ala Gly Lys Ile Ala Lys Ile Ala
                  5                    10
Gly Lys Ile Ala Lys Ile Ala Gly Lys Ile Ala
                15                      20

( 2 ) INFORMATION FOR SEQ ID NO:2:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:2:

Gly Ile Gly Lys Phe Leu Lys Lys Ala Lys
                  5                    10
Lys Phe Gly Lys Ala Phe Val Lys Ile Leu Lys Lys
                15                      20

( 2 ) INFORMATION FOR SEQ ID NO:3:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:3:

Gly Ile Gly Lys Phe Leu Lys Ser Ala Lys
                  5                    10
Lys Phe Gly Lys Ala Phe Val Lys Ile Met Asn Ser
                15                      20

( 2 ) INFORMATION FOR SEQ ID NO:4:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SER ID NO:4:

Gly Ile Gly Lys Phe Leu Lys Lys Ala Lys
                  5                    10
Lys Phe Gly Lys Ala Phe Val Lys Ile Met Lys Lys
                15                      20

( 2 ) INFORMATION FOR SEQ ID NO:5:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:5:

Lys Leu Ala Ser Lys Ala Gly Lys Ile Ala

```
                            5                      10
Gly  Lys  Ile  Ala  Lys  Val  Ala  Leu  Lys  Ala  Leu
                           15                      20
```

( 2 ) INFORMATION FOR SEQ ID NO:6:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:6:

```
Gly  Ile  Gly  Lys  Phe  Leu  Lys  Ser  Ala  Lys
                       5                       10
Lys  Phe  Gly  Lys  Ala  Phe  Val  Lys  Ile  Leu  Asn  Ser
                      15                      20
```

( 2 ) INFORMATION FOR SEQ ID NO:7:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:7:

```
Gly  Ile  Gly  Lys  Phe  Leu  Lys  Lys  Ala  Lys
                       5                       10
Lys  Phe  Ala  Lys  Ala  Phe  Val  Lys  Ile  Ile  Asn  Asn
                      15                      20
```

( 2 ) INFORMATION FOR SEQ ID NO:8:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION:
            Xaa is p- aminophenylalanine.

( x i ) SEQUENCE DESCRIPTION: SEQ ID NO:8:

```
Lys  Ile  Ala  Gly  Xaa  Ile  Ala  Lys  Ile  Ala
                       5                       10
Gly  Xaa  Ile  Ala  Lys  Ile  Ala  Gly  Xaa  Ile  Ala
                      15                      20
```

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:9:

```
Leu  Leu  Lys  Lys  Leu  Lys  Lys  Leu  Leu  Lys  Lys  Leu
```

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Lys Lys Leu Leu Lys Lys Leu Lys Lys Leu Leu Lys Lys Leu
               5                     10

(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Leu Lys Lys Leu Leu Lys Lys Leu Lys Lys Leu
           5               10